(12) United States Patent
Vassilev et al.

(10) Patent No.: US 8,889,146 B2
(45) Date of Patent: Nov. 18, 2014

(54) VACCINE

(75) Inventors: Ventzislav B. Vassilev, Rixensart (BE); Virginie Van Scherpenzeel Thim, Rixensart (BE); Normand Blais, Laval (CA); Patrick Rheault, Laval (CA)

(73) Assignee: GlaxoSmithKline Biologicals, SA, Rixensart (BE)

( * ) Notice: Subject to any disclaimer, the term of this patent is extended or adjusted under 35 U.S.C. 154(b) by 73 days.

(21) Appl. No.: 13/378,402

(22) PCT Filed: Jun. 24, 2010

(86) PCT No.: PCT/EP2010/059006
§ 371 (c)(1),
(2), (4) Date: Dec. 15, 2011

(87) PCT Pub. No.: WO2010/149743
PCT Pub. Date: Dec. 29, 2010

(65) Prior Publication Data
US 2012/0135028 A1    May 31, 2012

Related U.S. Application Data

(60) Provisional application No. 61/219,958, filed on Jun. 24, 2009.

(51) Int. Cl.
| A61K 39/295 | (2006.01) |
| A61K 39/155 | (2006.01) |
| C07K 14/005 | (2006.01) |
| A61K 39/17 | (2006.01) |
| A61K 39/00 | (2006.01) |

(52) U.S. Cl.
CPC ............ *A61K 39/155* (2013.01); *C07K 14/005* (2013.01); *C12N 2760/18534* (2013.01); *C07K 2319/73* (2013.01); *A61K 2039/55566* (2013.01); *C12N 2760/18522* (2013.01); *C12N 2760/18334* (2013.01); *C07K 2319/00* (2013.01); *A61K 2039/555* (2013.01); *C12N 2760/18622* (2013.01); *A61K 39/17* (2013.01); *C12N 2760/18634* (2013.01); *C12N 2760/18322* (2013.01)
USPC .................. 424/202.1; 424/185.1; 424/211.1; 435/5

(58) Field of Classification Search
CPC ... A61K 39/12; A61K 39/295; C07K 14/005; C07K 14/115; C07K 14/135
USPC .......... 424/184.1, 185.1, 186.1, 201.1, 211.1, 424/278.1
See application file for complete search history.

(56) References Cited

U.S. PATENT DOCUMENTS

| 4,436,727 | A |  | 3/1984 | Ribi |  |
| 4,866,034 | A |  | 9/1989 | Ribi |  |
| 4,877,611 | A |  | 10/1989 | Cantrel |  |
| 4,912,094 | A |  | 3/1990 | Myers |  |
| 5,057,540 | A |  | 10/1991 | Kensil et al. |  |
| 5,149,650 | A |  | 9/1992 | Wertz et al. |  |
| 5,750,110 | A |  | 5/1998 | Prieels et al. |  |
| 5,776,468 | A |  | 7/1998 | Hauser et al. |  |
| 6,113,911 | A |  | 9/2000 | Binz et al. |  |
| 6,245,549 | B1 | * | 6/2001 | Ewasyshyn et al. | ........ 435/235.1 |
| 7,208,161 | B1 |  | 4/2007 | Murphy et al. |  |
| 7,357,936 | B1 |  | 4/2008 | Garcon et al. |  |
| 7,368,537 | B2 |  | 5/2008 | Anderson et al. |  |
| 7,563,449 | B2 |  | 7/2009 | Ellsworth et al. |  |
| 8,563,002 | B2 | * | 10/2013 | Baudoux et al. | ............ 424/192.1 |
| 2006/0002958 | A1 | * | 1/2006 | Naylor | ........................ 424/209.1 |
| 2008/0300382 | A1 |  | 12/2008 | Libon et al. |  |
| 2010/0261155 | A1 | * | 10/2010 | Peeples et al. | ..................... 435/5 |
| 2010/0291147 | A1 | * | 11/2010 | Baudoux et al. | ............ 424/211.1 |
| 2011/0206758 | A1 |  | 8/2011 | Vandepapeliere et al. |  |
| 2012/0093847 | A1 |  | 4/2012 | Blais et al. |  |

FOREIGN PATENT DOCUMENTS

| EP | 0109942 | 3/1991 |
| EP | 0362279 | 1/1995 |
| EP | 0689454 | 9/1997 |
| GB | 2220211 | 1/1990 |
| WO | WO 93/06218 | 4/1993 |
| WO | WO 93/14207 | 7/1993 |
| WO | WO 94/21292 | 9/1994 |
| WO | WO 96/11711 | 4/1996 |
| WO | WO 96/33739 | 4/1997 |
| WO | WO 99/14334 | 3/1999 |
| WO | WO 02/42326 | 5/2002 |
| WO | WO 2005/027825 | 3/2005 |
| WO | WO 2006/038131 | 4/2006 |
| WO | WO 2008/114149 | 9/2008 |
| WO | WO 2009/021931 | 2/2009 |
| WO | WO 2009/079796 | 7/2009 |

OTHER PUBLICATIONS

Boivin, et al., "Global genetic diversity of human metapneumovirus fusion gene", EMERG. Infect. Dis. 10:1154-1157 (2004).
Calder, et al., "Electron microscopy of the human respiratory syncytial virus fusion protein and complexes that it forms with monoclonal antibodies", Virology, 271:122-131 (2000).
Connolly, et al, "Refolding a paramyxovirus F protein form prefusion to postfusion conformations observed by liposome binding and electron microscopy", Proceedings of The National Academy of Sciences of the United States, 103:17903-17908 (2006).

(Continued)

*Primary Examiner* — Stacy B Chen
(74) *Attorney, Agent, or Firm* — Gwynedd Warren

(57) ABSTRACT

The present disclosure provides immunogenic compositions that include at least two paramyxovirus F protein antigens selected from human metapnuemovirus (hMPV), paarainfluenza virus (PIV) and respiratory syncytial virus (RSV). The antigens of the disclosed compositions are recombinant F protein polypeptides, which have been modified to stabilize the trimeric prefusion conformation. Nucleic acids encoding the antigens, as well as methods for their production and use are also provided.

20 Claims, 12 Drawing Sheets

(56) References Cited

OTHER PUBLICATIONS

Cseke, et al., "Human metapneumovirus fusion protein vaccines that are immunogenic and protective in cotton rats", Journal of Virology, 81(2):698-707 (2007).

Dormitzer, et al., "Structure-based antigen design: a strategy for next generation vaccines", Trends in Biotechnology, 26(12):659-667 (2008).

Ewasyshyn, et al., "Comparative analysis of the immunostimulatory properties of different adjuvants on the immunogenicity of a prototype parainfluenza virus type 3 subunit vaccine", Vaccine, 10(6):412-420 (1992).

Gonzalez-Reyes, et al., "Cleavage of the human respiratory syncytial virus fusion protein at two distinct sites is required for activation of membrane fusion", Proceedings of the National Academy of Science USA, 98(7):9859-64 (2001).

Harbury, et al., "A switch between two-, three-, and four-stranded coiled coils in GCN4 leucine zipper mutants", Science, 262:1401-1407 (1993).

Herfst, et al., "Immunization of Syrian golden hamsters with F subunit vaccine of human metapneumovirus induces protection against challenge with homologous or heterologous strains", Journal of General Virology, 88(Part 10):2702-2709 (2007).

Martin, et al., "Sequence elements of the fusion peptide of human respiratory syncytial virus fusion protein required for activity", Journal of General Virology, 87(6):1649-58 (2006).

Mejias, et al., "New Approaches to reduce the burden of RSV infection", Drug Discovery Today: Therapeutic Strategies, 3(2):173-181 (2006).

Morton, et al., "Structural characterization of respiratory syncytial virus fusion inhibitor escape mutants: homology model of the F protein and a syncytium formation assay", Virology, 311:275-288 (2003).

Olson, et al., "Pulmonary immunity and immunopathology: lessons from respiratory syncytial virus", Expert Review of Vaccines, 7(8):1239-1255 (2008).

Prinoski, et al., "Evolution of the fusion protein gene of human parainfluenza virus", Virus Research, 22:55-69 (1991).

Sakurai, et al., "Human antibody responses to mature and immature forms of viral envelope in respiratory syncytial virus infection: significance for subunit vaccines", Journal of Virology, 73(4):2956-2692 (1999).

Schmidt, et al., "Mucosal immunization of rhesus monkeys against respiratory syncytial virus subgroups A and B and human parainfluenza virus type 3 by using a live cDNA-derived vaccine based on a host range-attenuated bovine parainfluenza virus type 3 vector backbone", Journal of Virology, 76(3):1089-99 (2002).

Tang, et al., "Parainfluenza virus type 3 expressing the native or soluble fusion (F) protein of respiratory syncytial virus (RSV) confers protection from RSV infection in African green monkeys", Journal of Virology, 78(20):11198-11207 (2004).

Ulbrandt, et al., "Identification of antibody neutralization epitopes on the fusion protein of human metapneumovirus", Journal of General Virology, 89(Part 12)3113-3118 (2008).

Valarcher, et al., "Bovine respiratory syncytial virus lacking the virokinin or with a mutation in furin cleavage site $RA(R/K)R^{109}$ induces less pulmonary inflammation without impeding the induction of protective immunity in calves", Journal of General Virology, 87(6):1659-1667 (2006).

Van Drunen Littel-van den Hurk, et al., "Immunopathology of RSV infection: prospects for developing vaccines without this complication", Reviews in Medical Virology, 17(1):5-34 (2007).

Walsh, et al., "Immunization with glycoprotein subunits of respiratory syncytial virus to protect cotton rats against viral infection", J. Infect. Dis., 155:1198-1204 (1987).

Yin, et al., "Structure of the parainfluenza virus 5 F protein in its metastable, prefusion conformation" Nature, 439(7072):38-44 (2006).

Yin, et al., "Structure of the uncleaved ectodomain of the paramyxovirus (hPIV3) fusion protein", Proceedings of the National Academy of Sciences of the United States, 102(26):9288-9293 (2005).

Zhang, et al., "Signal peptide prediction based on analysis of experimentally verified cleavage sites", Protein Sci., 13:2819-2824 (2004).

Zimmer, et al., "Cleavage at the furin consensus sequence RAR/KR109 and presence of the intervening peptide of the Respiratory Syncytial Virus fusion protein are dispensable for virus replication in cell culture", J. Virol. 76:9218-9224 (2002).

Zimmer, et al., "Proteolytic activation of Respiratory Syncytial Virus fusion protein", J. Biol. Chem. 276:31642-31650 (2001).

Haller, et al., "Bovine parainfluenza virus type 3 (PIV3) expressing the respiratory syncytial virus (RSV) attachment and fusion proteins protects hamsters from challenge with human PIV3 and RSV", Journal of General Virology, 84(8)2153-2162 (2003).

Yin, et al., "Structure of the parainfluenza virus 5F protein in its metastable prefusion conformation", Nature, 439(7072):38-44 (2006), including supplementary information retrieved from the internet; retrieved from http://www.nature.com.

Zhan, et al., "Sendai virus recombinant vaccine expressing hPIV-3 HN or F elicits protective immunity and combines with a second recombinant to prevent hPIV-1, hPIV-3 and RSV infections", Vaccine, 26:3480-3488 (2008).

* cited by examiner

Alignment of F protein sequences hPIV3 phylogenetic analysis
Fusion protein precursor
539aa

FIG. 5A

Fusion protein precursor 574aa

FIG. 5B

Percent Identity

| | 1 | 2 | 3 | 4 | 5 | 6 | 7 | 8 | 9 | 10 | 11 | 12 | 13 | 14 | 15 | |
|---|---|---|---|---|---|---|---|---|---|---|---|---|---|---|---|---|
| 1 | ■ | 89.4 | 89.4 | 89.2 | 89.4 | 89.4 | 89.5 | 89.2 | 89.2 | 89.2 | 89.0 | 89.2 | 89.4 | 89.2 | 89.2 | 1 | RSV-A2.pro
| 2 | 11.5 | ■ | 98.6 | 99.0 | 99.0 | 98.4 | 99.0 | 99.1 | 98.8 | 98.8 | 98.8 | 99.0 | 99.1 | 99.0 | 99.1 | 2 | RSV-B1.pro
| 3 | 11.5 | 1.4 | ■ | 99.3 | 99.3 | 98.8 | 99.3 | 99.0 | 99.3 | 99.3 | 99.1 | 99.3 | 99.5 | 98.6 | 98.8 | 3 | RSV-B-SAB4SA98D1656.pro
| 4 | 11.7 | 1.1 | 0.7 | ■ | 99.7 | 99.1 | 99.7 | 99.3 | 99.5 | 99.5 | 99.5 | 99.7 | 99.8 | 99.0 | 99.1 | 4 | RSV-B-GB3SA98D796.pro
| 5 | 11.5 | 1.1 | 0.7 | 0.3 | ■ | 99.1 | 99.7 | 99.3 | 99.5 | 99.5 | 99.5 | 99.7 | 99.8 | 99.0 | 99.1 | 5 | RSV-B-GB3SA98D941.pro
| 6 | 11.5 | 1.6 | 1.2 | 0.9 | 0.9 | ■ | 99.5 | 98.8 | 99.0 | 99.0 | 99.0 | 99.1 | 99.3 | 98.4 | 98.6 | 6 | RSV-B-GB4SA97D1107.pro
| 7 | 11.3 | 1.1 | 0.7 | 0.3 | 0.3 | 0.5 | ■ | 99.3 | 99.5 | 99.5 | 99.5 | 99.7 | 99.8 | 99.0 | 99.1 | 7 | RSV-B-GB4SA98VR468.pro
| 8 | 11.7 | 0.9 | 1.1 | 0.7 | 0.7 | 1.2 | 0.7 | ■ | 99.1 | 99.1 | 99.1 | 99.3 | 99.5 | 98.8 | 99.3 | 8 | RSV-B-RSV2177.pro
| 9 | 11.7 | 1.2 | 0.7 | 0.5 | 0.5 | 1.1 | 0.5 | 0.9 | ■ | 100.0 | 99.3 | 99.5 | 99.7 | 98.8 | 99.0 | 9 | RSV-B-SAB1SA010258K.pro
| 10 | 11.7 | 1.2 | 0.7 | 0.5 | 0.5 | 1.1 | 0.5 | 0.9 | 0.0 | ■ | 99.3 | 99.5 | 99.7 | 98.8 | 99.0 | 10 | RSV-B-SAB1SA0100258K.pro
| 11 | 11.9 | 1.2 | 0.9 | 0.5 | 0.5 | 1.1 | 0.5 | 0.9 | 0.7 | 0.7 | ■ | 99.5 | 99.7 | 98.8 | 99.0 | 11 | RSV-B-SAB2SA99V800.pro
| 12 | 11.7 | 1.1 | 0.7 | 0.3 | 0.3 | 0.9 | 0.3 | 0.7 | 0.5 | 0.5 | 0.5 | ■ | 99.8 | 99.1 | 99.1 | 12 | RSV-B-SAB3SA98VR192.pro
| 13 | 11.5 | 0.9 | 0.5 | 0.2 | 0.2 | 0.7 | 0.2 | 0.5 | 0.3 | 0.3 | 0.3 | 0.2 | ■ | 99.1 | 99.3 | 13 | RSV-B-SAB3SA010072K.pro
| 14 | 11.7 | 1.1 | 1.4 | 1.1 | 1.1 | 1.6 | 1.1 | 0.9 | 1.2 | 1.1 | 1.2 | 1.1 | 0.9 | ■ | 99.1 | 14 | RSV-18537.pro
| 15 | 11.7 | 0.9 | 1.2 | 0.9 | 0.9 | 1.4 | 0.9 | 0.7 | 1.1 | 1.1 | 1.1 | 0.9 | 0.7 | 0.9 | ■ | 15 | RSV-9320.pro
| | 1 | 2 | 3 | 4 | 5 | 6 | 7 | 8 | 9 | 10 | 11 | 12 | 13 | 14 | 15 | |

- Percent identity between subtype A strains: >96.7%
- Percent identity between subtype B strains: >98.4%

Serology in immunized mice, CHO-preF

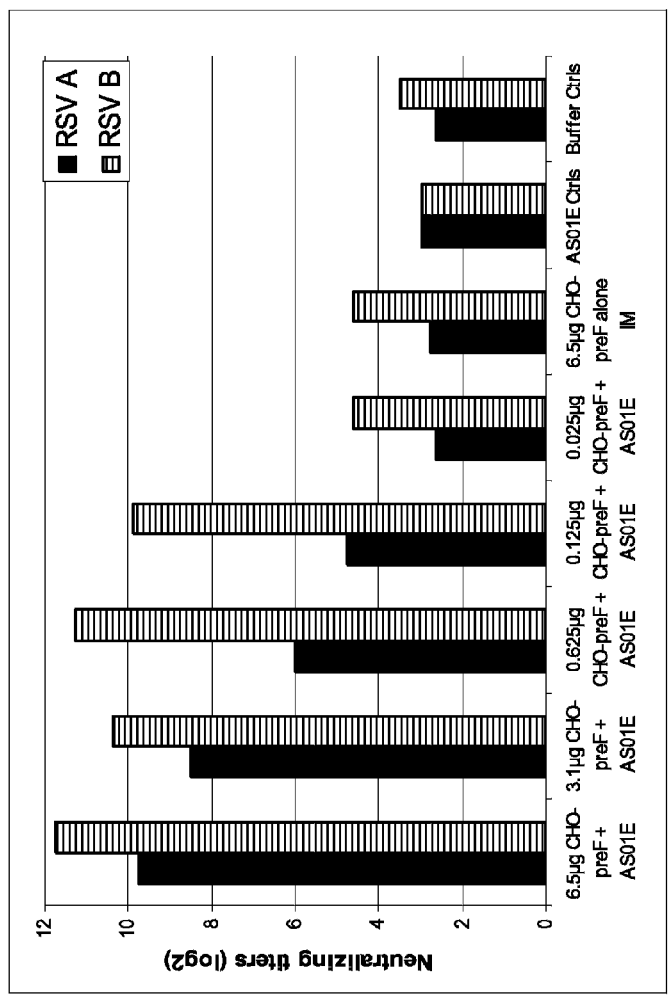

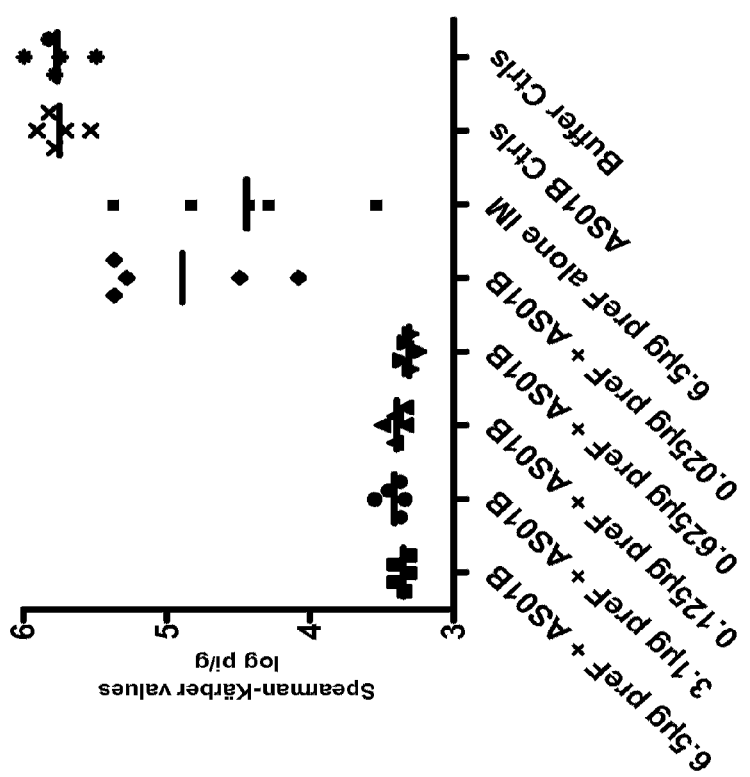

IgG Titers Elicited by PreF Antigens

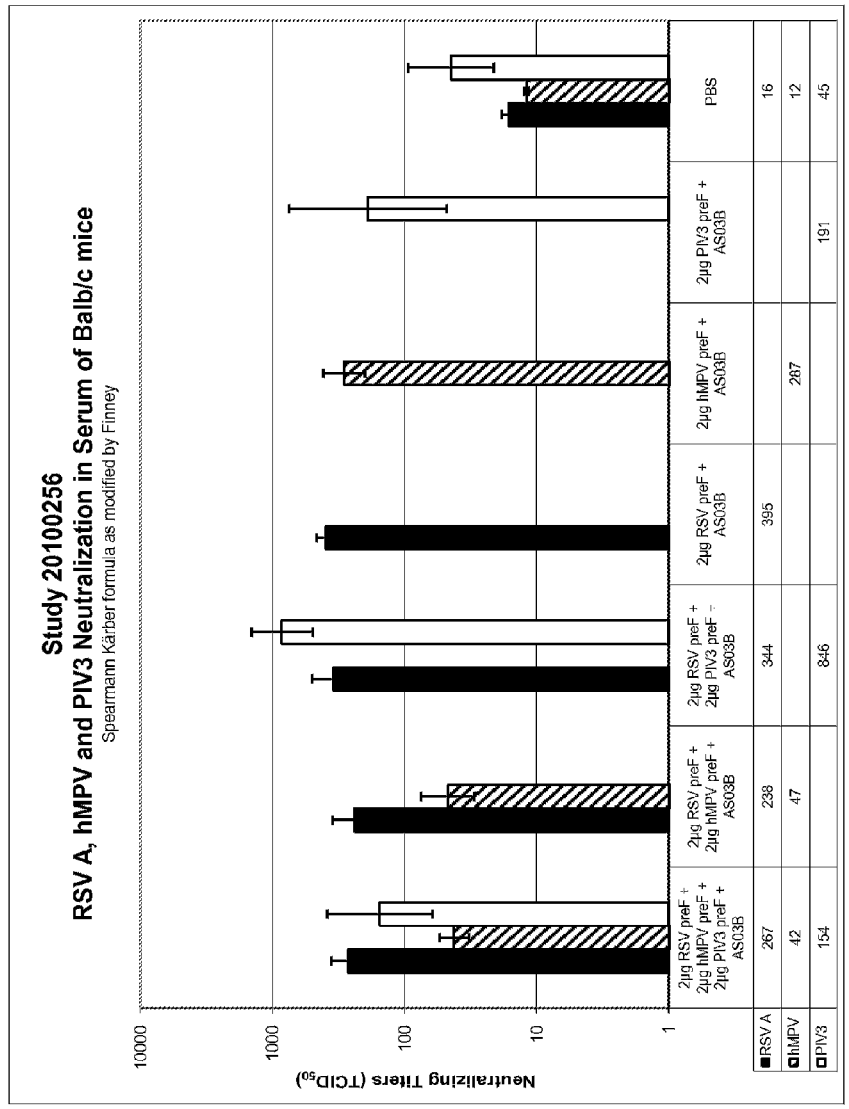

VACCINE

CROSS-REFERENCE TO RELATED APPLICATIONS

This application is the US National Stage of International Application No. PCT/EP2010/059006, filed 24 Jun. 2010, which claims benefit of the filing date of U.S. Provisional Application No. 61/219,958, filed 24 Jun. 2009. Both of these applications are incorporated herein by reference.

COPYRIGHT NOTIFICATION PURSUANT TO 37 C.F.R. §1.71(E)

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

This disclosure concerns the field of immunology. More particularly this disclosure relates to compositions and methods for eliciting an immune response that reduces infection and/or symptoms of infection by the leading causes of lower respiratory tract infection.

Human Respiratory Syncytial Virus (RSV), human Metapnumovirus (hMPV), and Parainfluenza viruses (PIV1-4) are the most common causes of lower respiratory tract infections (LRI) in infants less than one year of age. The spectrum of disease caused by these viruses includes a wide array of respiratory symptoms from rhinitis and otitis to pneumonia and bronchiolitis, the latter two diseases being associated with considerable morbidity and mortality.

Respiratory syncytial virus (RSV) is a pathogenic virus of the family Paramyxoviridae, subfamily Pneumovirinae, genus *Pneumovirus*. The genome of RSV is a negative-sense RNA molecule, which encodes 11 proteins. Tight association of the RNA genome with the viral N protein forms a nucleocapsid wrapped inside the viral envelope. Two groups of human RSV strains have been described, the A and B groups, based on differences in the antigenicity of the G glycoprotein.

Human metapneumovirus (hMPV), like human respiratory syncytial virus (RSV), is classified in the Pneumovirinae subfamily of the Paramyxoviridae family. However, hMPV is most closely genetically related to avian metapneumovirus (formerly called turkey rhinotracheitis virus). These two viruses are classified in the genus *Metapneumovirus*, with hMPV the first in this genus to cause disease in humans. hMPV was first described in 2001 by researchers in the Netherlands, and has since been identified in countries on all continents except Antarctica. hMPV is a single negative-stranded RNA-enveloped virus. Two major groups (A and B) and 4 subgroups of hMPV have been identified to date.

Human parainfluenza viruses are a group of paramyxoviruses that rank second only to respiratory syncytial virus (RSV) as a cause of lower respiratory tract disease in young children. Human parainfluenza viruses are classified in the Paramyxovirinae subfamily, *Respirovirus* genus. Like RSV, human parainfluenza viruses (HPIVs) can cause repeated infections throughout life. These infections are usually manifested by an upper respiratory tract illness (such as a cold or sore throat). HPIVs can also cause serious lower respiratory tract disease with repeat infection (including pneumonia, bronchitis, and bronchiolitis), especially among the elderly, and among patients with compromised immune systems. Each of the four HPIVs (serotypes 1-4) has different clinical and epidemiologic features. The most distinctive clinical feature of HPIV-1 and HPIV-2 is croup (laryngotracheobronchitis). HPIV-3 is most often associated with severe lower respiratory disease, including bronchiolitis and pneumonia. HPIV-4 is infrequently associated with severe disease.

Various approaches have been attempted in efforts to produce a safe and effective vaccines against these respiratory viruses that produces durable and protective immune responses in healthy and at risk populations. However, none of the candidates evaluated to date have been proven safe and effective as a vaccine for the purpose of preventing infection and/or reducing or preventing disease, including lower respiratory infections (LRIs), caused by these viruses.

BRIEF SUMMARY

This disclosure concerns immunogenic compositions that include at least two paramyxovirus F protein antigens selected from among the leading viral causes of lower respiratory tract infection in humans. The immunogenic compositions disclosed herein include at least two F protein antigens selected from metapneumovirus (hMPV), parainfluenza virus (PIV), and respiratory syncytial virus (RSV). The antigens in the combination are recombinant F proteins that have been modified to stabilize the trimeric prefusion conformation. Also disclosed are nucleic acids that encode the recombinant antigens, and methods for producing and using the antigens to elicit an immune response specific for at least two of these viruses, for example, to protect against infection and/or disease caused by infection with these agents.

BRIEF DESCRIPTION OF THE DRAWINGS

Figures 1A, 1B:
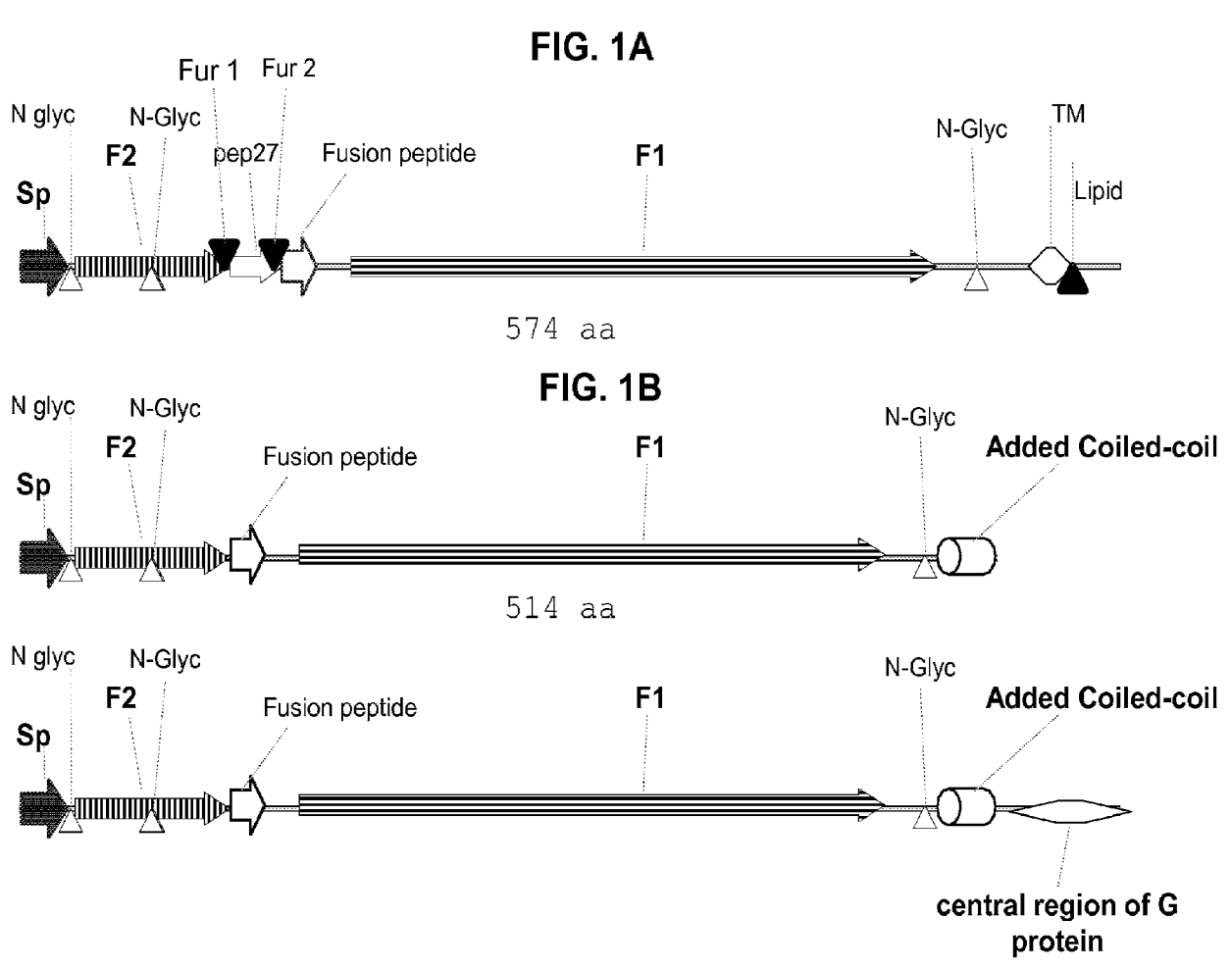

FIG. 1A is a schematic illustration highlighting structural features of the RSV F protein.

FIG. 1B is a schematic illustration of exemplary RSV Prefusion F (PreF) antigens.

Figure 2:
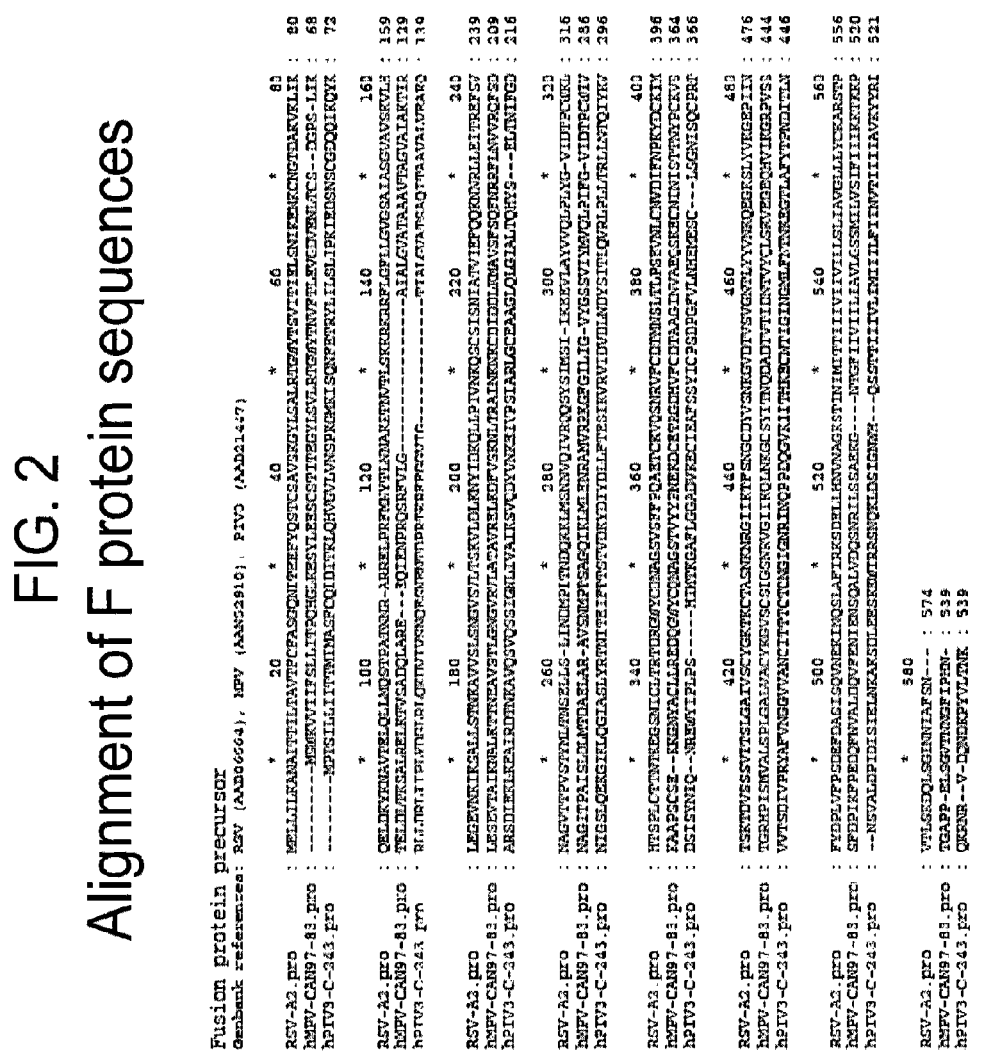

FIG. 2 is a sequence alignment between exemplary F protein polypeptides of RSV (SEQ ID NO:2), hMPV (SEQ ID NO:6) and PIV (SEQ ID NO:8).

Figure 5A:
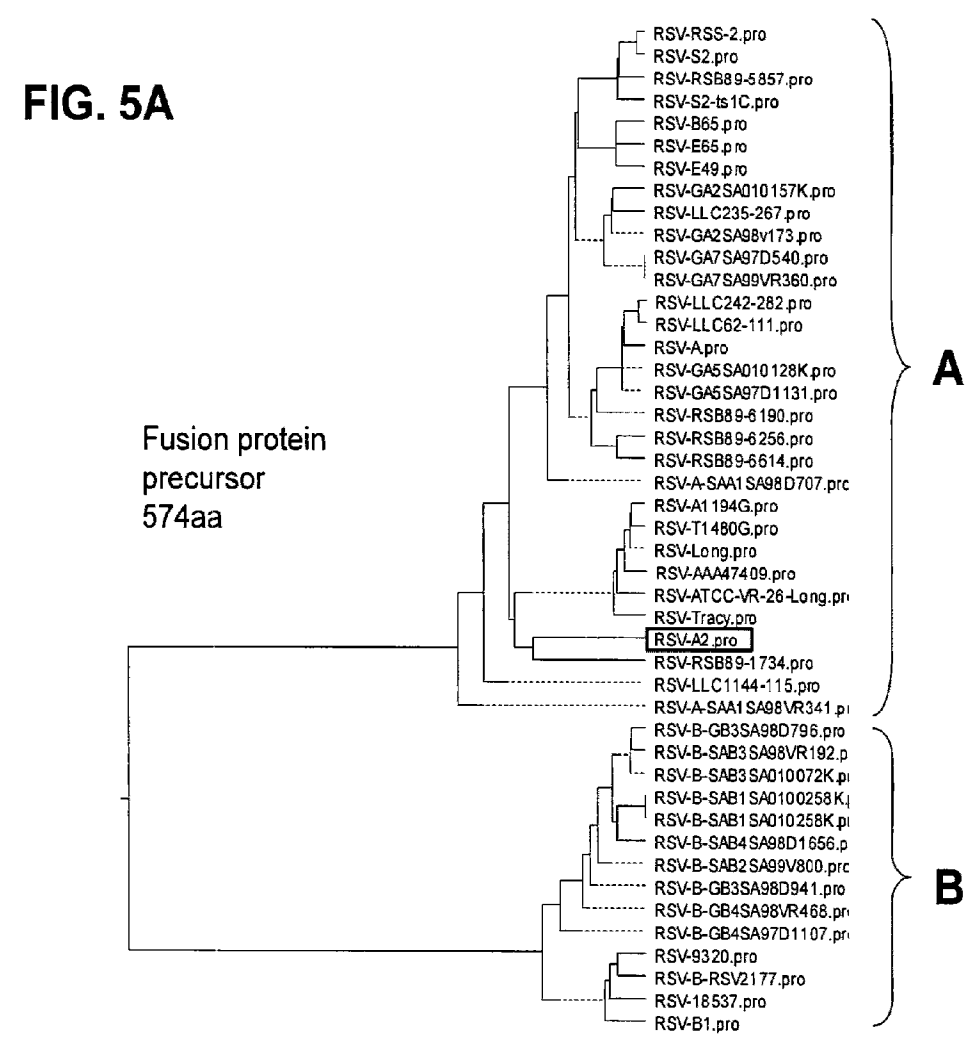

FIG. 5A is a phylogenic trees that illustrate relatedness of exemplary strains of RSV.

FIG. 5B is a summary table providing a pairwise comparison of % identity.

FIG. 7 is a graph showing protection against challenge provided by the RSV PreF antigen in mice.

DETAILED DESCRIPTION

Introduction

Figure 3A:
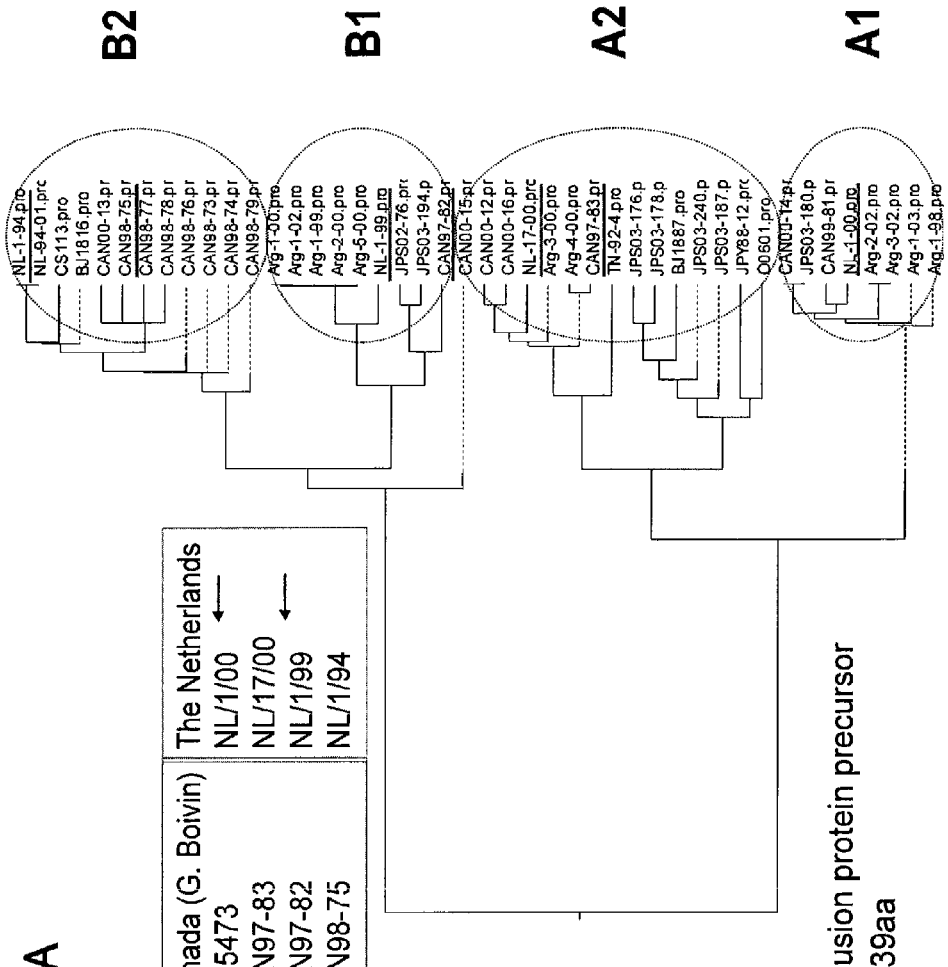
FIG. 3A is a phylogenic trees that illustrate relatedness of exemplary strains of hMPV.
Figure 3B:
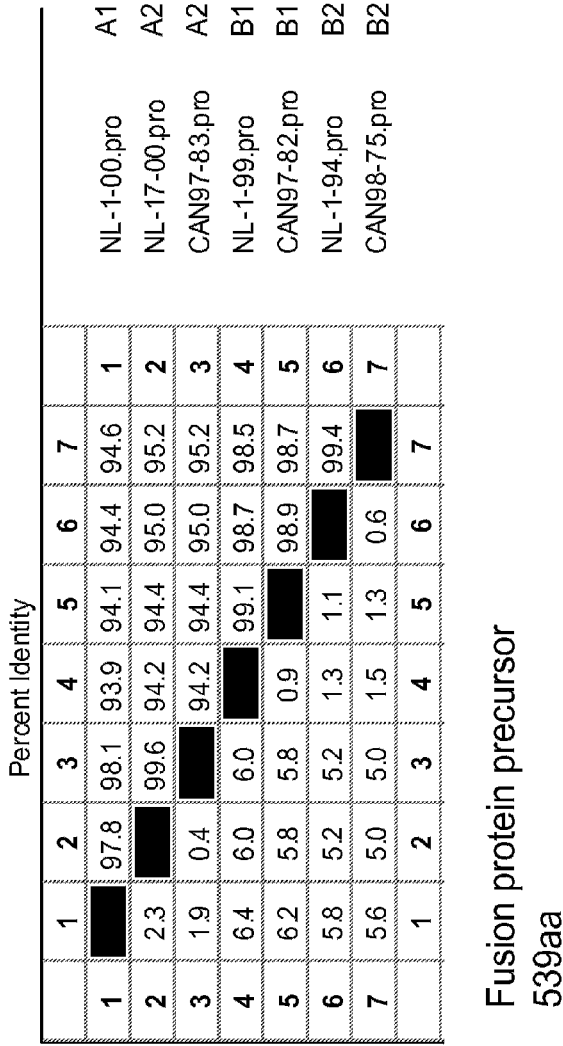
FIG. 3B is a summary table providing a pairwise comparison of % identity.
Figure 4A:
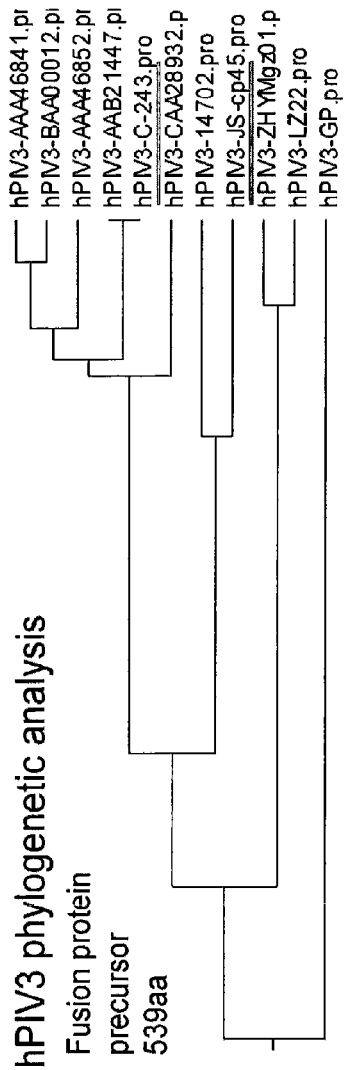
FIG. 4A is a phylogenic trees that illustrate relatedness of exemplary strains of PIV-3.
Figure 4B:
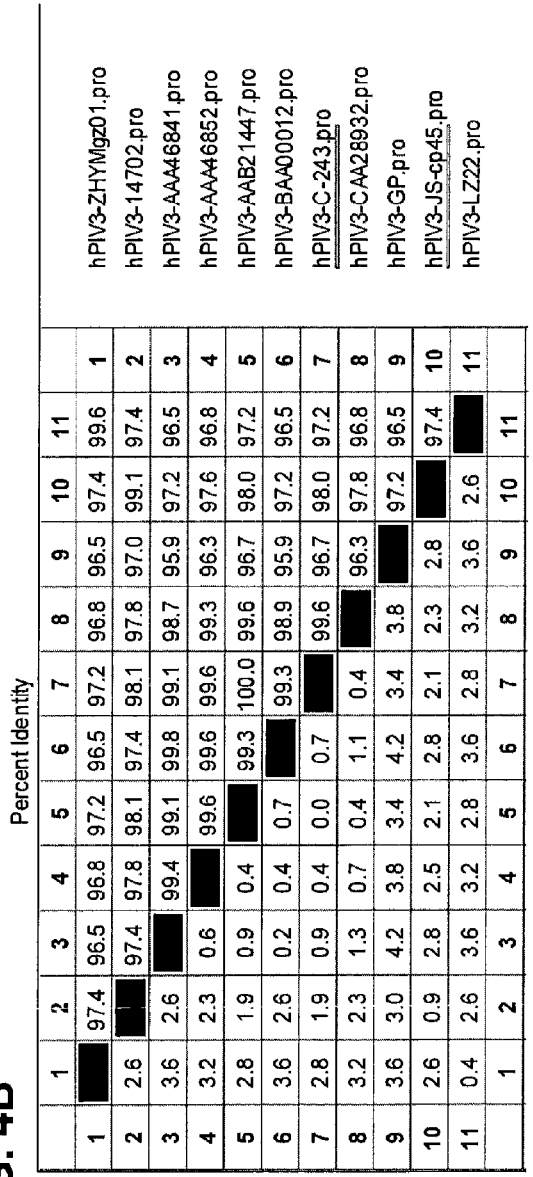
FIG. 4B is a summary table providing a pairwise comparison of % identity.

The three leading causes of lower respiratory tract infection, including severe manifestations such as bronchiolitis and pneumonia, in infants and young children are, in descending order, respiratory syncytial virus (RSV), human metapneumovirus (hMPV) and members of the parainfluenza virus (PIV) family. The present disclosure describes combination vaccines that protect against viral pathogens of the paramyxovirus family, and provides for an optimization of the immunization schedule to facilitate protection of very young infants in accordance with a vaccination schedule that is compatible with routine immunization.

WO2009/079796 (US 2010/0291147) discloses the design, production and utilization of novel antigens including a recombinant RSV F protein that has been modified to stabilize the trimeric prefusion conformation. The disclosed recombinant antigens exhibit superior immunogenicity, and are particularly favorably employed as components of immunogenic compositions (e.g., vaccines) for protection against RSV infection and/or disease. Also disclosed are nucleic acids that encode the recombinant antigens, immunogenic compositions containing the antigens, and methods for producing and using the antigens. The present disclosure extends these teachings to other paramyxoviruses responsible for human respiratory infections and disease. More specifically, the present disclosure provides recombinant hMPV and PIV (e.g., PIV-3) proteins that are similarly stabilized in the trimeric prefusion conformation. These antigens are particularly useful in compositions containing combinations of antigens to elicit an immune response that protects against or reduces the impact of infection by two or more paramyxoviruses.

One aspect of this disclosure relates to an immunogenic composition that includes at least two paramyxovirus F protein antigens selected from the group of: human metapneumovirus (hMPV), parainfluenza virus (PIV), and respiratory syncytial virus (RSV). The paramyxovirus F protein antigens are recombinant F protein polypeptides that include an F2 domain and an F1 domain of a paramyxovirus F protein polypeptide, lack a transmembrane domain (e.g., are soluble) and are stabilized in the trimeric prefusion conformation by a heterologous trimerization domain. For example, the heterologous trimerization domain can include a coiled-coil domain, such as an isoleucine zipper, as exemplified by the amino acid sequence of SEQ ID NO:15. Upon expression, the F protein polypeptides assemble into multimers, preferably trimers.

The F protein polypeptides typically include an F2 domain and an F1 domain with no intervening furin cleavage site. Such that the F2 and F1 domains are not cleaved during processing and in the mature form, the F protein polypeptide retains an intact fusion peptide between the F2 and F1 domains. Typically, the heterologous trimerization domain is positioned C-terminal to the F1 domain (e.g., in place of or within about 20 amino acids N-terminal to the position in which the transmembrane domain occurs in a naturally occurring paramyxovirus F protein).

Typically, the F protein polypeptides include a signal peptide (which can be cleaved from the mature antigen). The signal peptide can be from the same paramyxovirus F protein, from a different paramyxovirus F protein, or from a different protein altogether. For example, the signal peptide can be selected at the discretion of the practitioner to facilitate production in a selected host cell.

The F protein polypeptides stably assemble into trimers that are engineered to maintain the prefusion conformation. Optionally, the F protein polyeptpides also include one or more modification that enhances stability of the prefusion conformation. For example, favorable modifications include: substitutions or additions of a hydrophilic amino acid in a hydrophobic domain of the F protein extracellular domain (e.g., HRA and/or HRB); and substitution of an amino acid that alters glycosylation. Optionally, the F protein polypeptide includes a polyhistidine sequence or other tag to facilitate purification.

In certain embodiments, the immunogenic compositions also include at least one paramyxovirus G protein polypeptide or immunogenic fragment thereof. The G protein polypeptide can be a full length recombinant G protein, or an isolated immunogenic fragment or a chimeric (or "fusion") protein (either to a F protein polypeptide or to another fusion partner) When a fragment is selected, the fragment typically retains at least one immunodominant epitope, e.g., amino acids 184-198 of the RSV G protein.

In certain embodiments, the immunogenic composition includes two paramyxovirus F protein antigens. For example, in one specific embodiment, the immunogenic composition includes a F protein polypeptide corresponding to a hMPV F protein and a F protein polypeptide corresponding to a PIV (e.g., PIV-3) F protein. In other embodiments, the immunogenic composition includes an RSV F protein polypeptide in combination with an hMPV F protein polypeptide or a PIV protein polypeptide, or both hMPV and PIV protein polypeptides. In other embodiments, the immunogenic composition includes, in addition to the at least two paramyxovirus F protein antigens, at least one additional antigen. For example, in addition to F protein polypeptides corresponding to RSV, hMPV and/or PIV, the immunogenic composition can also include an additional paramxyovirus antigen, such as an F protein polypeptide corresponding to a different RSV strain. Alternatively, the immunogenic composition can include a second (or more) PIV F protein antigen, such as a F protein polypeptide corresponding to a different serotype of PIV, for example, such that the composition includes antigens of PIV-3 and PIV-1. In other embodiments, the immunogenic composition includes a third or subsequent antigen from a virus, such as influenza (an orthomyxovirus), adenovirus or SARS, which are also responsible for respiratory tract infections. For example, the immunogenic composition can include, in addition to a hMPV F protein polypeptide and a PIV protein polypeptide and/or an RSV F protein polypeptide, an influenza HA antigen.

In certain favorable embodiments, the immunogenic compositions also include at least one carrier or excipient (for example, a buffer). The immunogenic compositions are favorably formulated with an adjuvant, preferably and adjuvant that elicits a Th1 biased immune response. The adjuvant is typically selected to enhance a protective immune response without causing undue reactogenicity in the target population, e.g., neonates and infants.

When administered to a subject, or population of subjects, the immunogenic compositions disclosed herein reduces or prevents infection with, and/or a pathological response caused by, two or more of hMPV, PIV and RSV, and optionally one or more additional respiratory pathogens. Thus, this disclosure provides methods for eliciting an immune response against one or more of hMPV, PIV and RSV by administering to a subject (e.g., a human subject) the immunogenic compositions disclosed herein. Administration of the disclosed immunogenic compositions favorably elicit a Th1 biased immune response that reduces or prevents infection by at least two of hMPV, PIV and RSV. Accordingly, this disclosure relates to the use of the paramyxovirus F protein antigens in the preparation of a medicament for treating (e.g., preventing) infections caused by two or more of hMPV, PIV and RSV. For example, the F protein antigens (or nucleic acids) are used in the preparation of medicaments for the purpose of prophylactically treating an infection caused by one or more of hMPV, PIV and RSV.

Another aspect of the present disclosure concerns recombinant nucleic acids that include a polynucleotide sequence that encodes the recombinant paramyxovirus F protein antigens disclosed herein. Such nucleic acids are frequently codon optimized for expression in a selected host cell. The nucleic acids can be inserted into a vector, such as a prokaryotic or eukaryotic expression vector. In certain embodiments, the nucleic acids are introduced into host cells. Host cells are favorably selected from among bacterial cells, insect cells, plant cells and mammalian cells.

Terms

Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, are intended to be approximate. Thus, where a concentration is indicated to be at least (for example) 200 pg, it is intended that the concentration be understood to be at least approximately (or "about" or "~") 200 pg.

Although methods and materials similar or equivalent to those described herein can be used in the practice or testing of this disclosure, suitable methods and materials are described below. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of terms are provided. Additional terms and explanations can be provided in the context of this disclosure.

The term "F protein" or "Fusion protein" or "F protein polypeptide" or Fusion protein polypeptide" refers to a polypeptide or protein having all or part of an amino acid sequence of a paramyxovirus Fusion protein polypeptide. Similarly, the term "G protein" or "G protein polypeptide" refers to a polypeptide or protein having all or part of an amino acid sequence of a paramyxovirus Attachment protein polypeptide. Numerous paramyxovirus Fusion and Attachment proteins have been described and are known to those of skill in the art. WO2008114149 sets out exemplary RSV F and G protein variants (for example, naturally occurring variants) publicly available as of the filing date of this disclosure. Exemplary strains of hMPV F protein are catalogued in Boivin et al. *Emerg. Infect. Dis.* 10:1154-1157 (2004), incorporated herein by reference for disclosure of hMPV sequences, and attached hereto as Appendix 1. Sequences of exemplary PIV (e.g., PIV-3) F proteins are provided in Prinoski et al. *Virus Research* 22:55-69 (1991), incorporated herein by reference for disclosure of PIV sequences, and attached hereto as Appendix 2. Each of these references is incorporated herein by reference for the purpose of disclosing exemplary F protein sequences. Additionally, many of these sequences are publicly available in the GenBank database (as of 24 Jun. 2009).

A "variant" when referring to a nucleic acid or a polypeptide (e.g., a paramyxovirus F or G protein nucleic acid or polypeptide or analogue) is a nucleic acid or a polypeptide that differs from a reference nucleic acid or polypeptide. Usually, the difference(s) between the variant and the reference nucleic acid or polypeptide constitute a proportionally small number of differences as compared to the referent.

A "domain" of a polypeptide or protein is a structurally defined element within the polypeptide or protein. For example, a "trimerization domain" is an amino acid sequence within a polypeptide that promotes assembly of the polypeptide into trimers. For example, a trimerization domain can promote assembly into trimers via associations with other trimerization domains (of additional polypeptides with the same or a different amino acid sequence). The term is also used to refer to a polynucleotide that encodes such a peptide or polypeptide.

The terms "native" and "naturally occurring" refer to an element, such as a protein, polypeptide, or nucleic acid, which is present in the same state as it is in nature. That is, the element has not been modified artificially. It will be understood, that in the context of this disclosure, there are numerous native/naturally occurring variants of RSV proteins or polypeptides, e.g., obtained from different naturally occurring strains or isolates of RSV.

The term "polypeptide" refers to a polymer in which the monomers are amino acid residues which are joined together through amide bonds. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "fragment," in reference to a polypeptide, refers to a portion (that is, a subsequence) of a polypeptide. The term "immunogenic fragment" refers to all fragments of a polypeptide that retain at least one predominant immunogenic epitope of the full-length reference protein or polypeptide. Orientation within a polypeptide is generally recited in an N-terminal to C-terminal direction, defined by the orientation of the amino and carboxy moieties of individual amino acids. Polypeptides are translated from the N or amino-terminus towards the C or carboxy-terminus.

A "signal peptide" is a short amino acid sequence (e.g., approximately 18-25 amino acids in length) that direct newly synthesized secretory or membrane proteins to and through membranes, e.g., of the endoplasmic reticulum. Signal peptides are frequently but not universally located at the N-terminus of a polypeptide, and are frequently cleaved off by signal peptidases after the protein has crossed the membrane. Signal sequences typically contain three common structural features: an N-terminal polar basic region (n-region), a hydrophobic core, and a hydrophilic c-region).

The terms "polynucleotide" and "nucleic acid sequence" refer to a polymeric form of nucleotides at least 10 bases in length. Nucleotides can be ribonucleotides, deoxyribonucleotides, or modified forms of either nucleotide. The term includes single and double forms of DNA. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. In one embodiment, a polynucleotide encodes a polypeptide. The 5' and 3' direction of a nucleic acid is defined by reference to the connectivity of individual nucleotide units, and designated in accordance with the carbon positions of the deoxyribose (or ribose) sugar ring. The informational (coding) content of a polynucleotide sequence is read in a 5' to 3' direction.

A "recombinant" nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. A "recombinant" protein is one that is encoded by a heterologous (e.g., recombinant) nucleic acid, which has been introduced into a host cell, such as a bacterial or eukaryotic cell. The nucleic acid can be introduced, on an expression vector having signals capable of expressing the protein encoded by the introduced nucleic acid or the nucleic acid can be integrated into the host cell chromosome.

The term "heterologous" with respect to a a nucleic acid, a polypeptide or another cellular component, indicates that the component occurs where it is not normally found in nature and/or that it originates from a different source or species.

The term "purification" (e.g., with respect to a pathogen or a composition containing a pathogen) refers to the process of removing components from a composition, the presence of which is not desired. Purification is a relative term, and does not require that all traces of the undesirable component be removed from the composition. In the context of vaccine production, purification includes such processes as centrifugation, dialization, ion-exchange chromatography, and size-exclusion chromatography, affinity-purification or precipitation. Thus, the term "purified" does not require absolute purity; rather, it is intended as a relative term. Thus, for example, a purified nucleic acid preparation is one in which the specified protein is more enriched than the nucleic acid is in its generative environment, for instance within a cell or in a biochemical reaction chamber. A preparation of substantially pure nucleic acid or protein can be purified such that the desired nucleic acid represents at least 50% of the total nucleic acid content of the preparation. In certain embodiments, a substantially pure nucleic acid will represent at least 60%, at least 70%, at least 80%, at least 85%, at least 90%, or at least 95% or more of the total nucleic acid or protein content of the preparation.

An "isolated" biological component (such as a nucleic acid molecule, protein or organelle) has been substantially separated or purified away from other biological components in the cell of the organism in which the component naturally occurs, such as, other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins.

An "antigen" is a compound, composition, or substance that can stimulate the production of antibodies and/or a T cell response in an animal, including compositions that are injected, absorbed or otherwise introduced into an animal. The term "antigen" includes all related antigenic epitopes. The term "epitope" or "antigenic determinant" refers to a site on an antigen to which B and/or T cells respond. The "dominant antigenic epitopes" or "dominant epitope" are those epitopes to which a functionally significant host immune response, e.g., an antibody response or a T-cell response, is made. Thus, with respect to a protective immune response against a pathogen, the dominant antigenic epitopes are those antigenic moieties that when recognized by the host immune system result in protection from disease caused by the pathogen. The term "T-cell epitope" refers to an epitope that when bound to an appropriate MHC molecule is specifically bound by a T cell (via a T cell receptor). A "B-cell epitope" is an epitope that is specifically bound by an antibody (or B cell receptor molecule).

An "adjuvant" is an agent that enhances the production of an immune response in a non-specific manner. Common adjuvants include suspensions of minerals (alum, aluminum hydroxide, aluminum phosphate) onto which antigen is adsorbed; emulsions, including water-in-oil, and oil-in-water (and variants thereof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components.

An "immunogenic composition" is a composition of matter suitable for administration to a human or animal subject (e.g., in an experimental setting) that is capable of eliciting a specific immune response, e.g., against a pathogen, such as hMPV, PIV (e.g., PIV-3, PIV-1), and/or RSV. As such, an immunogenic composition includes one or more antigens (for example, polypeptide antigens) or antigenic epitopes. An immunogenic composition can also include one or more additional components capable of eliciting or enhancing an immune response, such as an excipient, carrier, and/or adjuvant. In certain instances, immunogenic compositions are administered to elicit an immune response that protects the subject against symptoms or conditions induced by a pathogen. In some cases, symptoms or disease caused by a pathogen is prevented (or reduced or ameliorated) by inhibiting replication of the pathogen (e.g., hMPV, a PIV, and/or RSV) following exposure of the subject to the pathogen. In the context of this disclosure, the term immunogenic composition will be understood to encompass compositions that are intended for administration to a subject or population of subjects for the purpose of eliciting a protective or palliative immune response against the pathogen (that is, vaccine compositions or vaccines).

An "immune response" is a response of a cell of the immune system, such as a B cell, T cell, or monocyte, to a stimulus. An immune response can be a B cell response, which results in the production of specific antibodies, such as antigen specific neutralizing antibodies. An immune response can also be a T cell response, such as a CD4+ response or a CD8+ response. In some cases, the response is specific for a particular antigen (that is, an "antigen-specific response"). If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo.

A "Th1" biased immune response is characterized by the presence of CD4+ T helper cells that produce IL-2 and IFN-γ, and thus, by the secretion or presence of IL-2 and IFN-γ. In contrast, a "Th2" biased immune response is characterized by a preponderance of CD4+ helper cells that produce IL-4, IL-5, and IL-13.

An "immunologically effective amount" is a quantity of a composition (typically, an immunogenic composition) used to elicit an immune response in a subject to the composition or to an antigen in the composition. Commonly, the desired result is the production of an antigen (e.g., pathogen)-specific immune response that is capable of or contributes to protecting the subject against the pathogen. However, to obtain a protective immune response against a pathogen can require multiple administrations of the immunogenic composition. Thus, in the context of this disclosure, the term immunologically effective amount encompasses a fractional dose that contributes in combination with previous or subsequent administrations to attaining a protective immune response.

The adjective "pharmaceutically acceptable" indicates that the referent is suitable for administration to a subject (e.g., a human or animal subject). Remington's Pharmaceutical Sciences, by E. W. Martin, Mack Publishing Co., Easton, Pa., 15th Edition (1975), describes compositions and formulations (including diluents) suitable for pharmaceutical delivery of therapeutic and/or prophylactic compositions, including immunogenic compositions.

The term "modulate" in reference to a response, such as an immune response, means to alter or vary the onset, magnitude, duration or characteristics of the response. An agent that modulates an immune response alters at least one of the onset, magnitude, duration or characteristics of an immune response following its administration, or that alters at least one of the onset, magnitude, duration or characteristic as compared to a reference agent.

The term "reduces" is a relative term, such that an agent reduces a response or condition if the response or condition is quantitatively diminished following administration of the agent, or if it is diminished following administration of the agent, as compared to a reference agent. Similarly, the term "prevents" does not necessarily mean that an agent completely eliminates the response or condition, so long as at least one characteristic of the response or condition is eliminated. Thus, an immunogenic composition that reduces or prevents an infection or a response, such as a pathological response, e.g., vaccine enhanced viral disease, can, but does not necessarily completely eliminate such an infection or response, so long as the infection or response is measurably diminished, for example, by at least about 50%, such as by at least about 70%, or about 80%, or even by about 90% of (that is to 10% or less than) the infection or response in the absence of the agent, or in comparison to a reference agent.

A "subject" is a living multi-cellular vertebrate organism. In the context of this disclosure, the subject can be an experimental subject, such as a non-human animal, e.g., a mouse, a cotton rat, or a non-human primate. Alternatively, the subject can be a human subject.

PreF Antigens

In nature, paramyxovirus F proteins are expressed as a single polypeptide precursor designated F0. In vivo, F0 oligomerizes in the endoplasmic reticulum and is proteolytically processed by a furin protease to generate an oligomer consisting of two disulfide-linked fragments. Whereas the RSV F F0 precursor is cleaved at two furin recognition sites, releasing an intervening peptide designated pep27, F proteins of other paramyxoviruses (including the PIV and hMPV F proteins) are cleaved at a single site. The smaller of the two fragments produced by furin cleavage is termed F2 and originates from the N-terminal portion of the F0 precursor. The larger, C-terminal F1 fragment anchors the F protein in the membrane via a sequence of hydrophobic amino acids, which are adjacent to a 24 amino acid cytoplasmic tail. It will be recognized by those of skill in the art that the abbreviations F0, F1 and F2 are commonly designated $F_0$, $F_1$ and $F_2$ in the scientific literature.

Three F2-F1 dimers associate to form a mature F protein, which adopts a metastable prefusogenic ("prefusion") conformation that is triggered to undergo a conformational change upon contact with a target cell membrane. This conformational change exposes a hydrophobic sequence, know as the fusion peptide, which associates with the host cell membrane and promotes fusion of the membrane of the virus, or an infected cell, with the target cell membrane.

The F1 fragment contains at least two heptad repeat domains, designated HRA and HRB, and situated in proximity to the fusion peptide and transmembrane anchor domains, respectively. In the prefusion conformation, the F2-F1 dimer forms a globular head and stalk structure, in which the HRA domains are in a segmented (extended) conformation in the globular head. In contrast, the HRB domains form a three-stranded coiled coil stalk extending from the head region. During transition from the prefusion to the postfusion conformations, the HRA domains collapse and are brought into proximity to the HRB domains to form an anti-parallel six helix bundle. In the postfusion state the fusion peptide and transmembrane domains are juxtaposed to facilitate membrane fusion.

Although the conformational description provided above is based on molecular modeling of crystallographic data, the structural distinctions between the prefusion and postfusion conformations can be monitored without resort to crystallography. For example, electron micrography can be used to distinguish between the prefusion and postfusion (alternatively designated prefusogenic and fusogenic) conformations, as demonstrated by Calder et al., Virology, 271:122-131 (2000) and Morton et al., Virology, 311:275-288, which are incorporated herein by reference for the purpose of their technological teachings. The prefusion conformation can also be distinguished from the fusogenic (postfusion) conformation by liposome association assays as described by Connolly et al., Proc. Natl. Acad. Sci. USA, 103:17903-17908 (2006), which is also incorporated herein by reference for the purpose of its technological teachings. Additionally, prefusion and fusogenic conformations can be distinguished using antibodies (e.g., monoclonal antibodies) that specifically recognize conformation epitopes present on one or the other of the prefusion or fusogenic form of a paramyxovirus F protein, but not on the other form. Such conformation epitopes can be due to preferential exposure of an antigenic determinant on the surface of the molecule. Alternatively, conformational epitopes can arise from the juxtaposition of amino acids that are non-contiguous in the linear polypeptide.

The PreF antigens disclosed herein are designed to stabilize and maintain the prefusion conformation of the paramyxovirus F protein, such that in a population of expressed protein, a substantial portion of the population of expressed protein is in the prefusogenic (prefusion) conformation (e.g., as predicted by structural and/or thermodynamic modeling or as assessed by one or more of the methods disclosed above). Stabilizing modifications are introduced into a native (or synthetic) F protein, such as the exemplary RSV F protein of SEQ ID NO:2, the exemplary hMPV protein of SEQ ID NO: 6 and/or the exemplary PIV protein of SEQ ID NO:8. Introduction of the disclosed stabilizing modifications results in maintenance of the major immunogenic epitopes of the prefusion conformation following introduction of the PreF antigen into a cellular or extracellular environment (for example, in vivo, e.g., following administration to a subject).

First, a heterologous stabilizing domain can be placed at the C-terminal end of the construct in order to replace the membrane anchoring domain of the F0 polypeptide. This stabilizing domain is predicted to compensate for the HRB instability, helping to stabilize the—prefusion conformer. In exemplary embodiments, the heterologous stabilizing domain is a protein multimerization domain. One particularly favorable example of such a protein multimerization domain is a trimerization domain. Exemplary trimerization domains fold into a coiled-coil that promotes assembly into trimers of multiple polypeptides having such coiled-coil domains. One favorable example of a trimerization domain is an isoleucine zipper. An exemplary isoleucine zipper domain is the engineered yeast GCN4 isoleucine variant described by Harbury et al. *Science* 262:1401-1407 (1993). The sequence of one suitable isoleucine zipper domain is represented by SEQ ID NO:15, although variants of this sequence that retain the ability to form a coiled-coil stabilizing domain are equally suitable. Alternative stabilizing coiled coil trimerization domains include: TRAF2 (GENBANK® Accession No. Q12933 [gi:23503103]; amino acids 299-348); Thrombospondin 1 (Accession No. PO7996 [gi:135717]; amino acids 291-314); Matrilin-4 (Accession No. O95460 [gi:14548117]; amino acids 594-618; CMP (matrilin-1) (Accession No. NP_002370 [gi:4505111]; amino acids 463-496; HSF1 (Accession No. AAX42211 [gi:61362386]; amino acids 165-191; and Cubilin (Accession No. NP_001072 [gi:4557503]; amino acids 104-138. It is expected that a suitable trimerization domain results in the assembly of a substantial portion of the expressed protein into trimers. For example, at least 50% of a recombinant PreF polypeptide having a trimerization domain will assemble into a trimer (e.g., as assessed by AFF-MALS). Typically, at least 60%, more favorably at least 70%, and most desirably at least about 75% or more of the expressed polypeptide exists as a trimer.

In order to further enhance stability, a neutral residue within HRB (such as leucine, isoleucine, or valine) can be substituted by a polar residue (such as lysine, arginine, or glutamine). For example, in the context of an RSV PreF antigen, the leucine residue located at position 512 (relative to the native F0 protein) of the PreF can be substituted by a lysine (L482K of the exemplary PreF antigen polypeptide of SEQ ID NO:10). This substitution improves the coiled coil hydrophobic residue periodicity. Similarly, a lysine can be added following the amino acid at position 105. Corresponding or comparable residues can be selected in hMPV and PIV-3 F proteins by those of ordinary skill in the art.

In addition, deletion of the (one in the case of hMPV and PIV, and one or both in the case of RSV) furin cleavage motif(s) further stabilizes the prefusion conformer. With this design, the fusion peptide is not cleaved from F2, preventing release from the globular head of the prefusion conformer and accessibility to nearby membranes. Interaction between the fusion peptide and the membrane interface is predicted to be a major issue in the prefusion state instability. During the fusion process, interaction between the fusion peptide and the target membrane results in the exposure of the fusion peptide from within the globular head structure, enhancing instability of the prefusion state and folding into post-fusion conformer. This conformation change enables the process of membrane fusion. Removal of one (or optionally both, in the case of RSV) of the furin cleavage site(s) is predicted to prevent membrane accessibility to the N-terminal part of the fusion peptide, stabilizing the prefusion state. In the case of the RSV F protein, the sequence between the two furin cleavage sites, designated pep27 can also be removed. Thus, in exemplary embodiments disclosed herein, removal of the furin cleavage motif(s) results in a PreF antigen that comprises an intact fusion peptide, which is not cleaved by furin during or following processing and assembly.

Optionally, at least one non-furin cleavage site can also be removed, for example by substitution of one or more amino acids. For example, experimental evidence suggests that under conditions conducive to cleavage by certain metalloproteinases, the RSV PreF antigen can be cleaved in the vicinity of amino acids 110-118 (for example, with cleavage occurring between amino acids 112 and 113 of the PreF antigen; between a leucine at position 142 and glycine at position 143 of the reference F protein polypeptide of SEQ ID NO:2). Accordingly, modification of one or more amino acids within this region can reduce cleavage of the PreF antigen. For example, the leucine at position 112 can be substituted with a different amino acid, such as isoleucine, glutamine or tryptophan. Alternatively or additionally, the glycine at position 113 can be substituted by a serine or alanine Similar modifications can be made in the event that cleavage by non-furin proteases is observed during production of the hMPV and PIV PreF antigens.

Optionally, a PreF antigen can include one or more modifications that alters the glycosylation pattern or status (e.g., by increasing or decreasing the proportion of molecules glycosylated at one or more of the glycosylation sites present in a native F protein polypeptide. For example, the native RSV F protein polypeptide of SEQ ID NO:2 is predicted to be glycosylated at amino acid positions 27, 70 and 500 (corresponding to positions 27, 70 and 470 of the exemplary PreF antigen of SEQ ID NO:10). In an embodiment, a modification is introduced in the vicinity of the glycosylation site at amino acid position 500 (designated N470). For example, the glycosylation site can be removed by substituting an amino acid, such as glutamine (Q) in place of the asparagine at position 500 (of the reference sequence, which corresponds by alignment to position 470 of the exemplary PreF antigen). Favorably, a modification that increases glycosylation efficiency at this glycosylation site is introduced. Examples of suitable modifications include at positions 500-502, the following amino acid sequences: NGS; NKS; NGT; NKT. Interestingly, it has been found that modifications of this glycosylation site that result in increased glycosylation also result in substantially increased PreF production. Thus, in certain embodiments, the PreF antigens have a modified glycosylation site at the position corresponding to amino acid 500 of the reference PreF sequence (SEQ ID NO:2), e.g., at position 470 of the PreF antigen exemplified by SEQ ID NO:10). Suitable, modifications include the sequences: NGS; NKS; NGT; NKT at amino acids corresponding to positions 500-502 of the reference F protein polypeptide sequence. Similarly, glycosylation sites can be modified in the hMPV and PIV PreF antigens, for example at amino acids corresponding to one or more of positions 57, 172 and/or 353 of the reference hMPV F protein polypeptide sequence of SEQ ID NO:6 and/or for example, at amino acids corresponding to one or more of positions 238, 359 and/or 446 of the reference PIV3 F protein polypeptide of SEQ ID NO:8.

Any one of the stabilizing modifications disclosed herein, e.g., addition of a heterologous stabilizing domain, such as a coiled-coil (for example, an isoleucine zipper domain), preferably situated at the C-terminal end of the PreF antigen; modification of a residue, such as leucine to lysine, in the hydrophobic HRB domain; removal of a furin cleavage motif; removal of a non-furin cleavage site; and/or modification of a glycosylation site can be employed in combination with any one or more (or up to all—in any desired combination) of the other stabilizing modifications. For example, in an RSV PreF antigen, a heterologous coiled-coil (or other heterologous stabilizing domain) can be utilized alone or in combination with any of: a modification in a hydrophobic region, and/or removal of pep27, and/or removal of one or both furin cleavage site, and/or removal of a non-furin cleavage site, and/or modification of a glycosylation site. In certain specific embodiments, the RSV PreF antigen includes a C-terminal coiled-coil (isoleucine zipper) domain, a stabilizing substitution in the HRB hydrophobic domain, and removal of both furin cleavage sites. Such an embodiment lacks pep27 and includes an intact fusion peptide that is not removed by furin cleavage. In one specific embodiment, the PreF antigen also includes a modified glycosylation site at amino acid position 500. In an hMPV and/or PIV PreF antigen, a heterologous a heterologous coiled-coil (or other heterologous stabilizing domain) can be utilized alone or in combination with any of: a modification in a hydrophobic region, and/or removal of a furin cleavage site, and/or removal of a non-furin cleavage site, and/or modification of a glycosylation site. In certain specific embodiments, the hMPV or PIV PreF antigen includes a C-terminal coiled-coil (isoleucine zipper) domain, a stabilizing substitution in the HRB hydrophobic domain, and removal of the furin cleavage site. Such an embodiment includes an intact fusion peptide that is not removed by furin cleavage. Optionally, the hMPV or PIV PreF antigen also includes a modified glycosylation site.

The native F protein polypeptide can be selected from any F protein of the paramyxovirus for which a PreF antigen is desired. For example, in the case of RSV, an RSV A or RSV B strain, or from variants thereof (as defined above) can be selected. In certain exemplary embodiments, the F protein polypeptide is the F protein represented by SEQ ID NO:2. Numerous additional examples of F protein polypeptides from different RSV strains are disclosed in WO2008114149 (which is incorporated herein by reference for the purpose of providing additional examples of RSV F and G protein sequences).

In the case of hMPV, any A or B (e.g., A1, A2, B1, B2) strain, or from variants thereof (as defined above) can be selected. In certain exemplary embodiments, the hMPV F protein polypeptide is the F protein represented by SEQ ID NO:6. Numerous additional examples of F protein polypeptides from different hMPV strains are disclosed in Boivin et al. *Emerg. Infect. Dis.* 10:1154-1157 (2004), which is incorporated herein for the purpose of disclosing exemplary hMPV F protein sequences. Exemplary nucleic acid sequences can be readily identified by reference to the GenBank database.

In the case of PIV, any strain selected from serotypes 1-4, or from variants thereof (as defined above) can be selected. For example, in a composition designed to prevent lower respiratory tract disease, the PIV is most commonly a strain of PIV-3. In certain exemplary embodiments, the PIV F protein polypeptide is the F protein represented by SEQ ID NO:8. Sequences of additional PIV (e.g., PIV-3) fusion proteins are provided in Prinoski et al. *Virus Research* 22:55-69 (1991), which is incorporated herein for the purpose of disclosing exemplary PIV F protein sequences. Exemplary nucleic acid sequences can be readily identified by reference to the GenBank database.

To facilitate understanding of this disclosure, all amino acid residue positions, regardless of strain, are given with respect to (that is, the amino acid residue position corresponds to) the amino acid position of one of the exemplary F protein. Comparable amino acid positions of any other paramyxovirus can be determined easily by those of ordinary skill in the art by aligning the amino acid sequences of the selected virus F protein with that of the exemplary sequence using readily available and well-known alignment algorithms (such as BLAST, e.g., using default parameters). Additional variants of these or any other paramyxovirus F protein can arise through genetic drift, or can be produced artificially using site directed or random mutagenesis, or by recombination of two or more preexisting variants. Such additional variants are also suitable in the context of the PreF (and PreF-G) antigens disclosed herein.

In selecting F2 and F1 domains of the F protein, one of skill in the art will recognize that it is not strictly necessary to include the entire F2 and/or F1 domain. Typically, conformational considerations are of importance when selecting a subsequence (or fragment) of the F2 domain. Thus, the F2 domain typically includes a portion of the F2 domain that facilitates assembly and stability of the polypeptide. As disclosed in WO2009/079796 (US 2010/0291147), in certain embodiments involving an RSV F protein, the F2 domain includes amino acids 26-105. In certain exemplary embodiments involving an hMPV F protein, the F2 domain includes amino acids 19-98. In certain exemplary embodiments involving a PIV F protein, the F2 domain includes amino acids 19-105. However, variants having minor modifications in length (by addition, or deletion of one or more amino acids) are also possible.

Typically, at least a subsequence (or fragment) of the F1 domain is selected and designed to maintain a stable conformation that includes immunodominant epitopes of the F protein. In exemplary embodiments involving an RSV F protein, an F1 domain polypeptide comprises at least about amino acids 262-436 of an RSV F protein polypeptide. In one non-limiting example provided herein, the F1 domain comprises amino acids 137 to 516 of a native F protein polypeptide. One of skill in the art will recognize that additional shorter subsequences can be used at the discretion of the practitioner. In exemplary embodiments involving an hMPV F protein, the F1 domain includes amino acids 103-480 (e.g., 103-481), and in exemplary embodiments involving a PIV F protein, the F1 domain includes amino acids 110-481 (e.g., 110-484).

When selecting a subsequence of the F2 or F1 domain (or as will be discussed below with respect to the G protein component of certain PreF-G antigens), in addition to conformational consideration, it can be desirable to choose sequences (e.g., variants, subsequences, and the like) based on the inclusion of additional immunogenic epitopes. For example, additional T cell epitopes can be identified using anchor motifs or other methods, such as neural net or polynomial determinations, known in the art, see, e.g., RANKPEP (available on the world wide web at: mif.dfci.harvard.edu/Tools/rankpep.html); ProPred1 (available on the world wide web at: imtech.res.in/raghava/propredfindex.html); Bimas (available on the world wide web at: www-bimas.dcrt.nih-.gov/molbi/hla_bind/index.html); and SYFPEITH (available on the world wide web at: syfpeithi.bmi-heidelberg.com/ scripts/MHCServer.dll/home.htm). For example, algorithms are used to determine the "binding threshold" of peptides, and to select those with scores that give them a high probability of MHC or antibody binding at a certain affinity. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. Anchor residues are conserved residues that provide a contact point with the MHC molecule. T cell epitopes identified by such predictive methods can be confirmed by measuring their binding to a specific MHC protein and by their ability to stimulate T cells when presented in the context of the MHC protein.

Favorably, the PreF antigens (including PreF-G antigens as discussed below) include a signal peptide corresponding to the expression system, for example, a mammalian or viral signal peptide, such as an RSV F0 native signal sequence (e.g., amino acids 1-25 of SEQ ID NO:2 or amino acids 1-25 of SEQ ID NO:10), or an hMPV or PIV native signal sequence (e.g., amino acids 1-18 of SEQ ID NOs:6 or 8). Typically, the signal peptide is selected to be compatible with the cells selected for recombinant expression. For example, a signal peptide (such as a baculovirus signal peptide, or the melittin signal peptide, can be substituted for expression, in insect cells. Suitable plant signal peptides are known in the art, if a plant expression system is preferred. Numerous exemplary signal peptides are known in the art, (see, e.g., see Zhang & Henzel, *Protein Sci.*, 13:2819-2824 (2004), which describes numerous human signal peptides) and are catalogued, e.g., in the SPdb signal peptide database, which includes signal sequences of archaea, prokaryotes and eukaryotes (http://proline.bic.nus.edu.sg/spdb/). Optionally, any of the preceding antigens can include an additional sequence or tag, such as a His-tag to facilitate purification.

Optionally, the PreF antigen can include additional immunogenic components. In certain particularly favorable embodiments, the PreF antigen includes a paramyxovirus G protein antigenic component. Exemplary chimeric proteins having a PreF and G component from RSV are described in detail in WO2009/079796 (US 2010/0291147), which is incorporated herein in its entirety with respect to the detailed description of exemplary chimeric PreF-G proteins. Comparable PreF-G proteins can be designed and produced for any paramyxovirus, including specifically hMPV and PIV (e.g., PIV-3).

For example, with respect to selection of sequences corresponding to naturally occurring strains, one or more of the domains can correspond in sequence to an RSV A or B strain, such as the common laboratory isolates designated A2 or Long, or any other naturally occurring strain or isolate (as disclosed in the aforementioned WO2008114149). Similarly, sequences can be selected that correspond to other naturally occurring paramyxoviruses, including, for example, hMPV and PIV (as disclosed in the aforementioned Boivin et al. *Emerg. Infect. Dis.* 10:1154-1157 (2004) and Prinoski et al. *Virus Research* 22:55-69 (1991), respectively). Exemplary PreF protein polypeptides are provided in SEQ ID NOs: 10, 12, and 14 (RSV, hMPV and PIV-3, respectively).

In addition to such naturally occurring and isolated variants, engineered variants that share sequence similarity with the aforementioned sequences can also be employed in the context of PreF (including PreF-G) antigens. It will be understood by those of skill in the art, that the similarity between PreF antigen polypeptide (and polynucleotide sequences as described below), as for polypeptide (and nucleotide sequences in general), can be expressed in terms of the similarity between the sequences, otherwise referred to as sequence identity. Sequence identity is frequently measured in terms of percentage identity (or similarity); the higher the percentage, the more similar are the primary structures of the two sequences. In general, the more similar the primary structures of two amino acid (or polynucleotide) sequences, the more similar are the higher order structures resulting from folding and assembly. Variants of a PreF polypeptide (and polynucleotide) sequences typically have one or a small number of amino acid deletions, additions or substitutions but will nonetheless share a very high percentage of their amino acid, and generally their polynucleotide sequence. More importantly, the variants retain the structural and, thus, conformational attributes of the reference sequences disclosed herein. Thus, PreF protein polypeptides having 1, 2, 3, 4, 5 or up to 10 amino acid additions, deletions and/or substitutions relative to one of the exemplary PreF sequences of SEQ ID NOs:10, 12 and 14 are also embodiments of PreF protein polypeptides as disclosed herein. For example, a suitable embodiment includes an RSV, hMPV and/or PIV-3 PreF protein (e.g. of SEQ ID NOs: 10, 12 and/or 14) with an amino acid substitution that modifies a glycosylation site (as discussed above). Similarly, a suitable embodiment can include a substitution of an amino acid that alters an internal peptidase cleavage site (as discussed above) with respect to SEQ ID NOs:10, 12 and/or 14. In certain embodiments the PreF polypeptides include both such modifications relative to SEQ ID NOs:10, 12 and 14.

Methods of determining sequence identity are well known in the art, and are applicable to PreF antigen polypeptides, as well as the nucleic acids that encode them (e.g., as described below). Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations. The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

In some instances, the PreF antigens has one or more amino acid modification relative to the amino acid sequence of the naturally occurring strain from which it is derived (e.g., in addition to the aforementioned stabilizing modifications). Such differences can be an addition, deletion or substitution of one or more amino acids. A variant typically differs by no more than about 1%, or 2%, or 3%, or 4%, or 5%, or 6%, or 10%, or 15%, or 20% of the amino acid residues. For example, a variant PreF antigen (including PreF-G) polypeptide sequence can include 1, or 2, or up to 5, or up to about 10, or up to about 15, or up to about 50, or up to about 100 amino acid differences as compared to the exemplary PreF antigen polypeptide sequences of SEQ ID NO:10, or analogous PreF antigens based on the hMPV and/or PIV sequences (such as the exemplary sequences of SEQ ID NOs:12 and 14). Thus, a variant in the context of an F or G protein, or PreF antigen (including PreF-G antigen), typically shares at least 80%, or 85%, more commonly, at least about 90% or more, such as 94%, or 95%, or 96%, or 97%, or even 98% or 99% sequence identity with a reference protein, or any of the exemplary PreF antigens disclosed herein. Additional variants included as a feature of this disclosure are PreF antigens (including PreF-G antigens) that include all or part of a nucleotide or amino acid sequence selected from the naturally occurring variants disclosed in WO2008114149 (RSV), Boivin et al. *Emerg. Infect. Dis.* 10:1154-1157 (2004) (hMPV) and Prinoski et al. *Virus Research* 22:55-69 (1991) (PIV). For example, in certain embodiments, the RSV PreF polypeptide has at least 89% sequence identity to SEQ ID NO:10; the hMPV PreF polypeptide has at least 94% sequence identity to SEQ ID NO:12; and the PIV PreF polypeptide has at least 95% sequence identity to SEQ ID NO:14. Additional variants can arise through genetic drift, or can be produced artificially using site directed or random mutagenesis, or by recombination of two or more preexisting variants. Such additional variants are also suitable in the context of the PreF (and PreF-G) antigens disclosed herein. For example, the modification can be a substitution of one or more amino acids (such as two amino acids, three amino acids, four amino acids, five amino acids, up to about ten amino acids, or more) that do not alter the conformation or immunogenic epitopes of the resulting PreF antigen.

Alternatively or additionally, the modification can include a deletion of one or more amino acids and/or an addition of one or more amino acids. Indeed, if desired, one or more of the polypeptide domains can be a synthetic polypeptide that does not correspond to any single strain, but includes component subsequences from multiple strains, or even from a consensus sequence deduced by aligning multiple strains of paramyxovirus virus polypeptides. In certain embodiments, one or more of the polypeptide domains is modified by the addition of an amino acid sequence that constitutes a tag, which facilitates subsequent processing or purification. Such a tag can be an antigenic or epitope tag, an enzymatic tag or a polyhistidine tag. Typically the tag is situated at one or the other end of the protein, such as at the C-terminus or N-terminus of the antigen or fusion protein.

Nucleic Acids that Encode PreF Antigens

Another aspect of this disclosure concerns recombinant nucleic acids that encode PreF antigens as described above. More explicitly, such nucleic acids encode polypeptides that include a F protein polypeptide antigen that includes an F2 domain and an F1 domain of an paramyxovirus F protein polypeptide, which includes at least one modification selected from: (i) an addition of an amino acid sequence comprising a heterologous trimerization domain; (ii) a deletion of at least one furin cleavage site; (iii) a deletion of at least one non-furin cleavage site; and, (iv) at least one substitution or addition of a hydrophilic amino acid in a hydrophobic domain of the F protein extracellular domain. Optionally, such a polynucleotide encodes a PreF antigen with a modification in a glycosylation site. Additionally, in the case of an RSV PreF antigen, the modifications can also include deletion of one or more amino acids of the pep27 domain. The nature and structural details of such polypeptides are disclosed in detail above. One of skill in the art will readily be able to determine nucleotide sequences that encode any and all of the described polypeptide sequences based on the teachings herein, including the exemplary sequences provided in the sequence listing, and otherwise included (e.g., by incorporation by reference) in this disclosure.

In certain embodiments, the recombinant nucleic acids are codon optimized for expression in a selected prokaryotic or eukaryotic host cell. Details of codon optimized nucleic acids that encode PreF antigens, and which have been codon optimized for expression in mammalian, e.g., CHO, cells, are provided in WO2009/079796 (US 2010/0291147), which is incorporated herein by reference. To facilitate replication and expression, the nucleic acids can be incorporated into a vector, such as a prokaryotic or a eukaryotic expression vector. Host cells including recombinant paramyxovirus PreF antigen-encoding nucleic acids are also a feature of this disclosure. Favorable host cells include prokaryotic (i.e., bacterial) host cells, such as *E. coli*, as well as numerous eukaryotic host cells, including fungal (e.g., yeast) cells, insect cells, and mammalian cells (such as CHO, VERO and HEK293cells).

To facilitate replication and expression, the nucleic acids can be incorporated into a vector, such as a prokaryotic or a eukaryotic expression vector. Although the nucleic acids disclosed herein can be included in any one of a variety of vectors (inclding, for example, bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others), most commonly the vector will be an expression vector suitable for generating polypeptide expression products. In an expression vector, the nucleic acid encoding the PreF antigen is typically arranged in proximity and orientation to an appropriate transcription control sequence (promoter, and optionally, one or more enhancers) to direct mRNA synthesis. That is, the polynucleotide sequence of interest is operably linked to an appropriate transcription control sequence. Examples of such promoters include: the immediate early promoter of CMV, LTR or SV40 promoter, polyhedrin promoter of baculovirus, *E. coli* lac or trp promoter, phage T7 and lambda $P_L$ promoter, and other promoters known to control expression of genes in prokaryotic or eukaryotic cells or their viruses. The expression vector typically also contains a ribosome binding site for translation initiation, and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture, or such as kanamycin, tetracycline or ampicillin resistance in *E. coli*.

The expression vector can also include additional expression elements, for example, to improve the efficiency of translation. These signals can include, e.g., an ATG initiation codon and adjacent sequences. In some cases, for example, a translation initiation codon and associated sequence elements are inserted into the appropriate expression vector simultaneously with the polynucleotide sequence of interest (e.g., a native start codon). In such cases, additional translational control signals are not required. However, in cases where only a polypeptide-coding sequence, or a portion thereof, is inserted, exogenous translational control signals, including an ATG initiation codon is provided for translation of the nucleic acid encoding PreF antigen. The initiation codon is placed in the correct reading frame to ensure translation of the polynucleotide sequence of interest. Exogenous transcriptional elements and initiation codons can be of various origins, both natural and synthetic. If desired, the efficiency of expression can be further increased by the inclusion of enhancers appropriate to the cell system in use (Scharf et al. *Results Probl Cell Differ* 20:125-62 (1994); Bitter et al. *Methods in Enzymol* 153:516-544 (1987)).

In some instances, the nucleic acid (such as a vector) that encodes the PreF antigen includes one or more additional sequence elements selected to increase and/or optimize expression of the PreF encoding nucleic acid when introduced into a host cell. For example, in certain embodiments, the nucleic acids that encode the PreF antigen include an intron sequence, such as a Human Herpesvirus 5 intron sequence. Introns have been repeatedly demonstrated to enhance expression of homologous and heterologous nucleic acids when appropriately positioned in a recombinant construct. Another class of expression-enhancing sequences includes an epigenetic element such as a Matrix Attachment Region (or MAR), or a similar epigenetic element, e.g., STAR elements (for example, such as those STAR elements disclosed in Otte et al., *Biotechnol. Prog.* 23:801-807, 2007). Without being bound by theory, MARs are believed to mediate the anchorage of a target DNA sequence to the nuclear matrix, generating chromatin loop domains that extend outwards from the heterochromatin cores. While MARs do not contain any obvious consensus or recognizable sequence, their most consistent feature appears to be an overall high A/T content, and C bases predominating on one strand. These regions appear to form bent secondary structures that may be prone to strand separation, and may include a core-unwinding element (CUE) that can serve as the nucleation point for strand separation. Several simple AT-rich sequence motifs have been associated with MAR sequences: e.g., the A-box, the T-box, DNA unwinding motifs, SATB1 binding sites (H-box, A/T/C25) and consensus Topoisomerase II sites for vertebrates or *Drosophila*. Exemplary MAR sequences are described in published US patent application no. 20070178469, and in international patent application no. WO02/074969 (which are incorporated herein by reference). Additional MAR sequences that can be used to enhance expression of a nucleic acid encoding a PreF antigen include chicken lysozyme MAR, MARp1-42, MARp1-6, MARp1-68, and MARpx-29, described in Girod et al., *Nature Methods,* 4:747-753, 2007 (disclosed in GenBank Accession Nos. EA423306, DI107030, DI106196, DI107561, and DI106512, respectively). One of skill will appreciate that expression can further be modulated be selecting a MAR that produces an intermediate level of enhancement, as is reported for MAR 1-9. If desired, alternative MAR sequences for increasing expression of a PreF antigen can be identified by searching sequence databases, for example, using software such as MAR-Finder (available on the web at futuresoft.org/MarFinder), SMARTest (available on the web at genomatix.de), or SMARScan I (Levitsky et al., *Bioinformatics* 15:582-592, 1999). In certain embodiments, the MAR is introduced (e.g., transfected) into the host cell on the same nucleic acid (e.g., vector) as the PreF antigen-encoding sequence. In an alternative embodiment, the MAR is introduced on a separate nucleic acid (e.g., in trans) and it can optionally cointegrate with the PreF antigen-encoding polynucleotide sequence.

Exemplary procedures sufficient to guide one of ordinary skill in the art through the production of recombinant PreF antigen nucleic acids can be found in Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology,* 4th ed., Wiley & Sons, 1999.

Exemplary nucleic acids that encode PreF antigen polypeptides are represented by SEQ ID NOs:9, and in WO2009/079796 (US 2010/0291147). Variants that include a modification in a glycosylation site, e.g., at the amino acid corresponding to position 500 of SEQ ID NO:2 can be produced by altering (e.g., mutating) the nucleotides in the vicinity of positions 1408-1414 (as compared, for example, to the polynucleotide sequence of SEQ ID NO:1). Suitable sequences of nucleotides to encode glycosylation variants (e.g., that increase glycosylation efficiency) include: aacgggt, aacaagt, aacggga, and aacaaga. Alternative sequences, such as cagcagt, which eliminate a glycosylation site are also possible. Additional variants of can be produced by assembling analogous F and G protein polypeptide sequences selected from any of the known (or subsequently) discovered paramxyoviruses, e.g., as disclosed in WO2008114149, or that encode variants as disclosed in Boivin et al. *Emerg. Infect. Dis.* 10:1154-1157 (2004) (hMPV) and Prinoski et al. *Virus Research* 22:55-69 (1991) (PIV). Exemplary polynucleotide sequences that encode hMPV and PIV PreF proteins are provided in SEQ ID NOs:11 and 13, respectively. Additional sequence variants that share sequence identity with the exemplary variants can be produced by those of skill in the art. Typically, the nucleic acid variants will encode polypeptides that differ by no more than 1%, or 2%, or 5%, or 10%, or 15%, or 20% of the amino acid residues. That is, the encoded polypeptides share at least 80%, or 85%, more commonly, at least about 90% or more, such as 95%, or even 98% or 99% sequence identity to one of SEQ ID NOs:9, 11 and 13. It will be immediately understood by those of skill in the art, that the polynucleotide sequences encoding the PreF polypeptides, can themselves share less sequence identity due to the redundancy of the genetic code. In some instances, the PreF antigens has one or more amino acid modification relative to the amino acid sequence of the naturally occurring strain from which it is derived (e.g., in addition to the aforementioned stabilizing modifications). Such differences can be an addition, deletion or substitution of one or more nucleotides or amino acids, respectively. A variant typically differs by no more than about 1%, or 2%, or 5%, or 10%, or 15%, or 20% or of the nucleotide residues. For example, a variant PreF antigen (including PreF-G) nucleic acid can include 1, or 2, or up to 5, or up to about 10, or up to about 15, or up to about 50, or up to about 100 nucleotide differences as compared to the exemplary PreF antigen nucleic acids of SEQ ID NO:9 or to analogous nucleic acids of the exemplary hMPV or PIV PreF sequences of SEQ ID NOs:11 and 13. Thus, a variant in the context of an RSV F or G protein, or PreF antigen (including PreF-G antigen) nucleic acid, typically shares at least 80%, or 85%, more commonly, at least about 90% or more, such as 95%, or even 98% or 99% sequence identity with a PreF protein polypeptide illustrated in SEQ ID NO:9, 11 or 13. Additional variants can arise through genetic drift, or can be produced artificially using site directed or random mutagenesis, or by recombination of two or more preexisting variants. Such additional variants are also suitable in the context of the PreF (and PreF-G) antigens disclosed herein.

In addition to the variant nucleic acids previously described, nucleic acids that hybridize to one or more of the exemplary nucleic acids represented by SEQ ID NOs:9, 11 or 13 (and/or to SEQ ID NOs:1, 3, and 5) can also be used in the context of nucleic acids that encode PreF antigens. One of skill in the art will appreciate that in addition to the % sequence identity measure discussed above, another indicia of sequence similarity between two nucleic acids is the ability to hybridize. The more similar are the sequences of the two nucleic acids, the more stringent the conditions at which they will hybridize. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ and/or Mg$^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N.Y., 2001; Tijssen, *Hybridization With Nucleic Acid Probes, Part I: Theory and Nucleic Acid Preparation*, Laboratory Techniques in Biochemistry and Molecular Biology, Elsevier Science Ltd., NY, N.Y., 1993 and Ausubel et al. *Short Protocols in Molecular Biology*, 4$^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" can be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast, nucleic acids that hybridize under "low stringency" conditions include those with much less sequence identity, or with sequence identity over only short subsequences of the nucleic acid. It will, therefore, be understood that the various variants of nucleic acids that are encompassed by this disclosure are able to hybridize to at least one of SEQ ID NOs: 1, 3, and 5 at least over the portions that encode the F2 domain and the F1 domain of the F protein. For example, such nucleic acids can hybridize over substantially the entire length of at least one of SEQ ID NOs: 9, 11 and/or 13.

In certain examples, the nucleic acids are introduced into cells via vectors suitable for introduction and expression in prokaryotic cells, e.g., *E. coli* cells. For example, a nucleic acid including a polynucleotide sequence that encodes a PreF antigen can be introduced into any of a variety of commercially available or proprietary vectors, such as the pET series of expression vectors (e.g., pET9b and pET2d). Expression of the coding sequence is inducible by IPTG, resulting in high levels of protein expression. The polynucleotide sequence encoding the PreF antigen is transcribed under the phage T7 promoter. Alternate vectors, such as pURV22 that include a heat-inducible lambda pL promoter are also suitable.

The expression vector is introduced (e.g., by electroporation) into a suitable bacterial host. Numerous suitable strains of *E. coli* are available and can be selected by one of skill in the art (for example, the Rosetta and BL21 (DE3) strains have proven favorable for expression of recombinant vectors containing polynucleotide sequences that encode PreF antigens.

More typically, the polynucleotides that encode the PreF antigens are incorporated into expression vectors that are suitable for introduction and expression in eukaryotic (e.g., insect or mammalian cells). Favorably, such nucleic acids are codon optimized for expression in the selected vector/host cell. In one exemplary embodiment, the polynucleotide sequence that encodes the PreF antigen is introduced into a vector, such as the pEE14 vector developped by Lonza Biologicals firm. The polypeptide is expressed under a constitutive promoter, such as the immediate early CMV (CytoMegaloVirus) promoter. Selection of the stably transfected cells expressing the polypeptide is made based on the ability of the transfected cells to grow in the absence of a glutamine source. Cells that have successfully integrated the pEE14 are able to grow in the absence of exogenous glutamine, because the pEE14 vector expresses the GS (Glutamine Synthetase) enzyme. Selected cells can be clonally expanded and characterized for expression of the desired PreF polypeptide.

In another example, the polynucleotide sequence that encodes the PreF antigen is introduced into insect cells using a Baculovirus Expression Vector System (BEVS). Recombinant baculovirus capable of infecting insect cells can be generated using commercially available vectors, kits and/or systems, such as the BD BaculoGold system from BD BioScience. Briefly, the polynucleotide sequence encoding the antigen is inserted into the pAcSG2 transfer vector. Then, host cells SF9 (*Spodoptera frugiperda*) are co-transfected by pAcSG2-chimeric plasmid and BD BaculoGold, containing the linearized genomic DNA of the baculovirus *Autographa californica nuclear polyhedrosis virus* (AcNPV). Following transfection, homologous recombination occurs between the pACSG2 plasmid and the Baculovirus genome to generate the recombinant virus. In one example, the PreF antigen is expressed under the regulatory control of the polyhedrin promoter (pH). Similar transfer vectors can be produced using other promoters, such as the basic (Ba) and p10 promoters. Similarly, alternative insect cells can be employed, such as SF21 which is closely related to the Sf9, and the High Five cell line derived from a cabbage looper, *Trichoplusia ni*.

Following transfection and induction of expression (according to the selected promoter and/or enhancers or other regulatory elements), the expressed polypeptides are recovered (e.g., purified or enriched) and renatured to ensure folding into an antigenically active prefusion conformation.

Methods of Producing RSV Antigenic Polypeptides

The PreF antigens (including PreF-G antigens, and also where applicable, G antigens) disclosed herein are produced using well established procedures for the expression and purification of recombinant proteins. Procedures sufficient to guide one of skill in the art can be found in the following references: Sambrook et al., *Molecular Cloning: A Laboratory Manual*, Cold Spring Harbor Laboratory Press, Cold Spring Harbor, N.Y., 200; and Ausubel et al. *Short Protocols in Molecular Biology*, 4$^{th}$ ed., John Wiley & Sons, Inc., 999. Additional and specific details are provided hereinbelow.

Recombinant nucleic acids that encode the PreF antigens (as described above) are introduced into host cells by any of a variety of well-known procedures, such as electroporation, liposome mediated transfection (e.g., using a commercially available liposomal transfection reagent, such as LIPOFECTAMINE™2000 or TRANSFECTINT™), Calcium phosphate precipitation, infection, transfection and the like, depending on the selection of vectors and host cells.

Host cells that include recombinant PreF antigen-encoding nucleic acids are, thus, also a feature of this disclosure. Favorable host cells include prokaryotic (i.e., bacterial) host cells, such as *E. coli*, as well as numerous eukaryotic host cells, including fungal (e.g., yeast, such as *Saccharomyces cerevisiae* and *Picchia pastoris*) cells, insect cells, plant cells, and mammalian cells (such as CHO and HEK293 cells). Recombinant PreF antigen nucleic acids are introduced (e.g., transduced, transformed or transfected) into host cells, for example, via a vector, such as an expression vector. As described above, the vector is most typically a plasmid, but such vectors can also be, for example, a viral particle, a phage, etc. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression, and will be apparent to those skilled in the art and in the references cited herein, including, e.g., Freshney (1994) *Culture of Animal Cells, a Manual of Basic Technique*, third edition, Wiley-Liss, New York and the references cited therein. Expression products corresponding to the nucleic acids of the invention can also be produced in non-animal cells such as plants, yeast, fungi, bacteria and the like. In addition to Sambrook, Berger and Ausubel, details regarding cell culture can be found in Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

In bacterial systems, a number of expression vectors can be selected depending upon the use intended for the expressed product. For example, when large quantities of a polypeptide or fragments thereof are needed for the production of antibodies, vectors which direct high level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., a polynucleotide of the invention as described above, can be ligated into the vector in-frame with sequences for the amino-terminal translation initiating Methionine and the subsequent 7 residues of beta-galactosidase producing a catalytically active beta galactosidase fusion protein; pIN vectors (Van Heeke & Schuster (1989) *J Biol Chem* 264:5503-5509); pET vectors (Novagen, Madison Wis.), in which the amino-terminal methionine is ligated in frame with a histidine tag; and the like.

Similarly, in yeast, such as *Saccharomyces cerevisiae*, a number of vectors containing constitutive or inducible promoters such as alpha factor, alcohol oxidase and PGH can be used for production of the desired expression products. For reviews, see Berger, Ausubel, and, e.g., Grant et al. (1987; *Methods in Enzymology* 153:516-544). In mammalian host cells, a number of expression systems, including both plasmis and viral-based systems, can be utilized.

A host cell is optionally chosen for its ability to modulate the expression of the inserted sequences or to process the expressed protein in the desired fashion. Such modifications of the protein include, but are not limited to, glycosylation, (as well as, e.g., acetylation, carboxylation, phosphorylation, lipidation and acylation). Post-translational processing for example, which cleaves a precursor form into a mature form of the protein (for example, by a furin protease) is optionally performed in the context of the host cell. Different host cells such as 3T3, COS, CHO, HeLa, BHK, MDCK, 293, WI38, etc. have specific cellular machinery and characteristic mechanisms for such post-translational activities and can be chosen to ensure the correct modification and processing of the introduced, foreign protein.

For long-term, high-yield production of recombinant PreF antigens disclosed herein, stable expression systems are typically used. For example, cell lines which stably express a PreF antigen polypeptide are introduced into the host cell using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection, and its presence allows growth and recovery of cells which successfully express the introduced sequences. For example, resistant groups or colonies of stably transformed cells can be proliferated using tissue culture techniques appropriate to the cell type. Host cells transformed with a nucleic acid encoding a PreF antigen are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. Optionally, the medium includes components and/or additives that decrease degradation of expressed proteins by proteinases. For example, the medium used for culturing cells to produce PreF antigen can include a protease inhibitor, such as a chelating agent or small molecule inhibitor (e.g., AZ11557272, AS111793, etc.), to reduce or eliminate undesired cleavage by cellular, or extracellular (e.g., matrix) proteinases. Optionally, the cells are cultured in serum free (and/or animal product-free) medium. The cells can be grown at a convenient scale for the purpose, e.g., in shaker flasks or bioreactors.

The secreted polypeptide product is then recovered from the culture medium. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art.

Expressed PreF antigens can be recovered and purified from recombinant cell cultures by any of a number of methods well known in the art, including ammonium sulfate or ethanol precipitation, acid extraction, filtration, ultrafiltration, centrifugation, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted above, a variety of purification methods are well known in the art, including, e.g., those set forth in Sandana (1997) *Bioseparation of Proteins*, Academic Press, Inc.; and Bollag et al. (1996) *Protein*

Methods, 2nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, U.K.; Scopes (1993) Protein Purification: Principles and Practice 3rd Edition Springer Verlag, NY; Janson and Ryden (1998) Protein Purification Principles, High Resolution Methods and Applications, Second Edition Wiley-VCH, NY; and Walker (1998) Protein Protocols on CD-ROM Humana Press, NJ.

In one exemplary embodiment, the PreF proteins are recovered from cells according to the following purification scheme. Following introduction of a recombinant nucleic acid encoding the PreF polypeptide into host CHO cells, transiently transfected host cells or expanded stable populations comprising the introduced polynucleotide sequence are grown in medium and under conditions suitable for growth at an acceptable scale for the desired purpose (e.g., as generally described in Freshney (1994) Culture of Animal Cells, a Manual of Basic Technique, third edition, Wiley-Liss, New York and the references cited therein). Typically, the cells are grown in serum-free medium at 37° C. and passaged at 2-3 day intervals in shake flasks or in bioreactors. New cultures established from cells expanded in these conditions, are typically carried out in bioreactors in serum-free medium and incubated at 27° C. with pO2 maintained at 20% for 5 to 7 days in order to produce the preF antigen.

To recover recombinant PreF antigen, the cell culture is centrifuged and the cell culture supernatant stored at minus 70° C. until further use. Following thawing of culture supernatants, the supernatants are diluted 2× with MilliQ water and adjusted to pH 6.0 with HCl. Diluted supernatant is loaded at 75 cm/h onto a 3 L CM Ceramic HyperD FF resin packed in BPG 140/500 column, equilibrated in 20 mM phosphate pH 6.0. After loading of the sample, equilibration buffer is processed through the column to get back to UV baseline. After washing with 5 column volumes (CV) of 25 mM phosphate pH 7.0 buffer, elution is performed using a 50 mM Phosphate pH 7.0 buffer containing 0.1 M NaCl.

The CM Hyper D eluate is diluted 3.3× with 20 mM phosphate, pH 7.0 to be processed onto a 270 ml Hydroxyapatite Type II column (packed in XK 50), equilibrated with 20 mM $PO_4$ (Na) buffer pH 7.0, at 50 mL/min. After washing the column with the equilibration buffer (~3 CV), elution is performed using a 20 mM $PO_4$ (Na) pH 7.0 buffer containing 0.5 M NaCl.

The HA eluate is processed at 15 mL/min (to respect a 10 minutes contact time with the resin), onto a 150 mL Capto Adhere column (packed in XK 26), equilibrated in 20 mM phosphate pH 7.0. After washing with 5 CV of 10 mM phosphate pH 7.0 containing 0.1 M arginine buffer, elution is performed using a 10 mM Phosphate pH 7.0 buffer containing 0.6 M arginine.

The Capto Adhere eluate is then concentrated approximately 10× for processing onto a preparative size exclusion chromatography (SEC) column. Concentration is performed using a 50 kD Pellicon polyethersulfone membrane. Before being processed onto the SEC column, the material is filtered through a PLANOVA 20N 100 cm² filter, used as a viral clearance step. This nanofiltration step can be either placed after or before concentration on Pellicon membrane.

Preparative SEC is then performed using a 500 mL Superdex 5200 column and 10 mM phosphate (Na/$K_2$), 160 mM NaCl, pH 6.5 buffer (corresponding to final buffer) as mobile phase. A volume of concentrated PreF corresponding to 5% of SEC column volume is loaded onto the resin at ~2.6 mL/min. Typically, fractions of 10 mL are collected. Analytical pools of fractions can be analyzed on SDS gel by silver staining and western blot anti HCP (Host cell proteins) if desired to optimize yields while minimizing HCP levels.

Purified bulk is obtained after filtration on 0.22 µm Millex filters (alternatively a Sterivex filter can be used). If desired the purified PreF antigen preparation can be stored at minus 70° C. prior to use.

Alternatively, PreF proteins can include a polyhistidine (e.g., six histidine) tag, which can be used to facilitate purification. For such histidine tagged PreF polypeptides, the following purification protocol can be employed. Prior to purification using immobilized metal ion affinity chromatography (IMAC), the cell culture supernatant is diluted twofold in buffer A (20 mm Bicine, pH8.5) and pH is adjusted to 8.5. The resulting solution is loaded on a Q sepharose FF column (GE Healthcare), e.g., of 23 ml of column volume, previously equilibrated with Buffer A. PreF proteins are captured on the column, along with some host cell contaminants. The culture media components that would interfere with the IMAC purification step are not retained and are eliminated in the flow through. The proteins are separated and eluted by a stepwise elution of 200 mM, 400 mM, 600 mM, 800 mM and 1M NaCl. PreF proteins of interest are eluted during the first step at 200 mM NaCl. Optionally, recovery can be monitored using SDS PAGE and western blotting using an anti His-tag antibody to detect the tagged PreF protein. Fractions can be pooled prior to continuing the purification.

The (pooled) PreF protein containing eluate is diluted threefold in buffer B (20 mM Bicine, 500 mM NaCl, pH8.3) and pH is adjusted to 8.3. The resulting solution is loaded on IMAC sepharose FF resin loaded with Nickel chloride (GE Healthcare) (e.g., of 5 ml of column volume), previously equilibrated with buffer B. PreF are bound to the resin and the majority of host cell contaminants are eluted in the flow through. The column is washed with 20 mM Imidazole in order to remove weakly bound contaminants. PreF proteins are eluted by a step elution of 250 mM Imidazole. SDS PAGE stained with coomassie blue and western blot anti His-tag can be performed to identify positive fractions.

The pool from IMAC can then be concentrated to a concentration of at least 150 µg/ml using a centricon concentration device (Millipore) and the protein can be dialysed in PBS buffer supplemented with 500 mM L-Arginine. Resulting protein is quantified using RCDC protein assay (BioRad) and stored at −70 or −80° C. until use.

Immunogenic Compositions and Methods

The PreF antigens disclosed herein are useful in the formulation of immunogenic compositions, especially those that include a combination of antigens from at least two different paramyxoviruses that are a significant cause of respiratory disease, including severe lower respiratory disease, in infants. Typically, such immunogenic compositions include at least two paramyxovirus and a pharmaceutically acceptable carrier or excipient. For example, in certain embodiments, the immunogenic compositions include an hMPV antigen and a PIV antigen, such as a PIV-3 antigen or a PIV-1 antigen. In other embodiments, the immunogenic compositions include an RSV antigen and either an hMPV antigen or a PIV antigen (e.g., a PIV-3 antigen or a PIV-1 antigen). In other embodiments, the immunogenic compositions include three antigens. For example, in certain embodiments, the immunogenic compositions include an hMPV antigen, a PIV antigen and an RSV antigen (for example, an hMPV antigen, a PIV-3 antigen and an RSV antigen). In another embodiment, the immunogenic compositions include an hMPV antigen and two different PIV antigens (such as a PIV-3 antigen and a PIV-1 antigen). Such compositions can optionally also include an RSV antigen. Preferable, as disclosed herein the antigens are paramyxovirus PreF antigens.

In certain embodiments, the immunogenic compositions are vaccines that reduce or prevent infection with at least two of hMPV, PIV (e.g., PIV-3) and RSV. In some embodiments, the immunogenic compositions are vaccines that reduce or prevent a pathological response following infection with at least two of hMPV, PIV (e.g., PIV-3) and RSV. Optionally, the immunogenic compositions containing at least two PreF antigens selected from different paramyxoviruses (e.g., selected from hMPV, PIV and RSV) are formulated with at least one additional antigen of a different pathogenic virus. For example, the pathogenic organism can another strain of paramyxovirus (e.g., PIV-1, where the first strain of PIV is PIV-3), or it can be a viral pathogen of the respiratory tract, other than a paramyxovirus, such as an influenza virus. In other embodiments, the additional antigens are selected to facilitate administration or reduce the number of inoculations required to protect a subject against a plurality of infectious organisms. For example, the antigen can be derived from any one or more of influenza, hepatitis B, diphtheria, tetanus, pertussis, *Hemophilus influenza, poliovirus, Streptococcus* or *Pneumococcus*, among others.

In certain embodiments, typically, embodiments in which the PreF antigen does not include a G protein component, the immunogenic composition can be formulated with one or more isolated, recombinant and/or purified paramyxovirus G protein. Numerous suitable G proteins have been described in the art, and include full length recombinant G proteins and chimeric proteins made up of a portion of the G protein (such as amino acids 128-229 or 130-230) and a fusion partner (such as thioredoxin), or a signal and/or leader sequence, that facilitates expression and/or purification. Exemplary RSV G proteins for use in admixture with a PreF antigen can be found in WO2009/079796 (US 2010/0291147), WO2008114149, U.S. Pat. No. 5,149,650, U.S. Pat. No. 6,113,911, US Published Application No. 20080300382, and U.S. Pat. No. 7,368,537, each of which is incorporated herein by reference.

Pharmaceutically acceptable carriers and excipients are well known and can be selected by those of skill in the art. For example, the carrier or excipient can favorably include a buffer. Optionally, the carrier or excipient also contains at least one component that stabilizes solubility and/or stability. Examples of solubilizing/stabilizing agents include detergents, for example, laurel sarcosine and/or tween. Alternative solubilizing/stabilizing agents include arginine, and glass forming polyols (such as sucrose, trehalose and the like). Numerous pharmaceutically acceptable carriers and/or pharmaceutically acceptable excipients are known in the art and are described, e.g., in *Remington's Pharmaceutical Sciences*, by E. W. Martin, Mack Publishing Co., Easton, Pa., 5th Edition (975).

Accordingly, suitable excipients and carriers can be selected by those of skill in the art to produce a formulation suitable for delivery to a subject by a selected route of administration.

Suitable excipients include, without limitation: glycerol, Polyethylene glycol (PEG), Sorbitol, Trehalose, N-lauroylsarcosine sodium salt, L-proline, Non detergent sulfobetaine, Guanidine hydrochloride, Urea, Trimethylamine oxide, KCl, $Ca^{2+}$, $Mg^{2+}$, $Mn^{2+}$, $Zn^{2+}$ and other divalent cation related salts, Dithiothreitol, Dithioerytrol, and β-mercaptoethanol. Other excipients can be detergents (including: Tween80, Tween20, Triton X-00, NP-40, Empigen BB, Octylglucoside, Lauroyl maltoside, Zwittergent 3-08, Zwittergent 3-0, Zwittergent 3-2, Zwittergent 3-4, Zwittergent 3-6, CHAPS, Sodium deoxycholate, Sodium dodecyl sulphate, Cetyltrimethylammonium bromide).

Optionally, the immunogenic compositions also include an adjuvant. In the context of an immunogenic composition suitable for administration to a subject for the purpose of eliciting a protective immune response against RSV, the adjuvant is selected to elicit a Th1 biased immune response.

The adjuvant is typically selected to enhance a Th1 biased immune response in the subject, or population of subjects, to whom the composition is administered. For example, when the immunogenic composition is to be administered to a subject of a particular age group susceptible to (or at increased risk of) RSV infection, the adjuvant is selected to be safe and effective in the subject or population of subjects. Thus, when formulating an immunogenic composition containing an RSV PreF antigen for administration in an elderly subject (such as a subject greater than 65 years of age), the adjuvant is selected to be safe and effective in elderly subjects. Similarly, when the immunogenic composition containing the PreF antigen is intended for administration in neonatal or infant subjects (such as subjects between birth and the age of two years), the adjuvant is selected to be safe and effective in neonates and infants.

Additionally, the adjuvant is typically selected to enhance a Th1 immune response when administered via a route of administration, by which the immunogenic composition is administered. For example, when formulating an immunogenic composition containing a PreF antigen for nasal administration, proteosome and protollin are favorable Th1-biasing adjuvants. In contrast, when the immunogenic composition is formulated for intramuscular administration, adjuvants including one or more of 3D-MPL, squalene (e.g., QS21), liposomes, and/or oil and water emulsions are favorably selected.

One suitable adjuvant for use in combination with PreF antigens is a non-toxic bacterial lipopolysaccharide derivative. An example of a suitable non-toxic derivative of lipid A, is monophosphoryl lipid A or more particularly 3-Deacylated monophoshoryl lipid A (3D-MPL). 3D-MPL is sold under the name MPL by GlaxoSmithKline Biologicals N.A., and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-γ (Th1) phenotype. 3D-MPL can be produced according to the methods disclosed in GB2220211 A. Chemically it is a mixture of 3-deacylated monophosphoryl lipid A with 3, 4, 5 or 6 acylated chains. In the compositions of the present invention small particle 3D-MPL can be used. Small particle 3D-MPL has a particle size such that it can be sterile-filtered through a 0.22 μm filter. Such preparations are described in WO94/21292.

A lipopolysaccharide, such as 3D-MPL, can be used at amounts between 1 and 50 μg, per human dose of the immunogenic composition. Such 3D-MPL can be used at a level of about 25 μg, for example between 20-30 μg, suitably between 21-29 μg or between 22 and 28 μg or between 23 and 27 μg or between 24 and 26 μg, or 25 μg. In another embodiment, the human dose of the immunogenic composition comprises 3D-MPL at a level of about 10 μg, for example between 5 and 15 μg, suitably between 6 and 14 μg, for example between 7 and 13 μg or between 8 and 12 μg or between 9 and 11 μg, or 10 μg. In a further embodiment, the human dose of the immunogenic composition comprises 3D-MPL at a level of about 5 μg, for example between 1 and 9 μg, or between 2 and 8 μg or suitably between 3 and 7 μg or 4 and μg, or 5 μg.

In other embodiments, the lipopolysaccharide can be a β(1-6) glucosamine disaccharide, as described in U.S. Pat. No. 6,005,099 and EP Patent No. 0 729 473 B1. One of skill in the art would be readily able to produce various lipopolysaccharides, such as 3D-MPL, based on the teachings of these references. Nonetheless, each of these references is incorporated herein by reference. In addition to the aforementioned immunostimulants (that are similar in structure to that of LPS or MPL or 3D-MPL), acylated monosaccharide and disaccharide derivatives that are a sub-portion to the above structure of MPL are also suitable adjuvants. In other embodiments, the adjuvant is a synthetic derivative of lipid A, some of which are described as TLR-4 agonists, and include, but are not limited to: OM174 (2-deoxy-6-o-[2-deoxy-2-[(R)-3-dodecanoyloxytetradecanoylamino]-4-o-phosphono-β-D-glucopyranosyl]-2-[(R)-3-hydroxytetradecanoylamino]-α-D-glucopyranosyldihydrogenphosphate), (WO 95/14026); OM 294 DP (3S,9R)—3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO 99/64301 and WO 00/0462); and OM 197 MP-Ac DP (3S-,9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127).

Other TLR4 ligands which can be used are alkyl Glucosaminide phosphates (AGPs) such as those disclosed in WO 98/50399 or U.S. Pat. No. 6,303,347 (processes for preparation of AGPs are also disclosed), suitably RC527 or RC529 or pharmaceutically acceptable salts of AGPs as disclosed in U.S. Pat. No. 6,764,840. Some AGPs are TLR4 agonists, and some are TLR4 antagonists. Both are thought to be useful as adjuvants.

Other suitable TLR-4 ligands, capable of causing a signaling response through TLR-4 (Sabroe et al, JI 2003 p1630-5) are, for example, lipopolysaccharide from gram-negative bacteria and its derivatives, or fragments thereof, in particular a non-toxic derivative of LPS (such as 3D-MPL). Other suitable TLR agonists are: heat shock protein (HSP) 10, 60, 65, 70, 75 or 90; surfactant Protein A, hyaluronan oligosaccharides, heparan sulphate fragments, fibronectin fragments, fibrinogen peptides and b-defensin-2, and muramyl dipeptide (MDP). In one embodiment the TLR agonist is HSP 60, 70 or 90. Other suitable TLR-4 ligands are as described in WO 2003/011223 and in WO 2003/099195, such as compound I, compound II and compound III disclosed on pages 4-5 of WO2003/011223 or on pages 3-4 of WO2003/099195 and in particular those compounds disclosed in WO2003/011223 as ER803022, ER803058, ER803732, ER804053, ER804057, ER804058, ER804059, ER804442, ER804680, and ER804764. For example, one suitable TLR-4 ligand is ER804057.

Additional TLR agonists are also useful as adjuvants. The term "TLR agonist" refers to an agent that is capable of causing a signaling response through a TLR signaling pathway, either as a direct ligand or indirectly through generation of endogenous or exogenous ligand. Such natural or synthetic TLR agonists can be used as alternative or additional adjuvants. A brief review of the role of TLRs as adjuvant receptors is provided in Kaisho & Akira, Biochimica et *Biophysica Acta* 1589:1-13, 2002. These potential adjuvants include, but are not limited to agonists for TLR2, TLR3, TLR7, TLR8 and TLR9. Accordingly, in one embodiment, the adjuvant and immunogenic composition further comprises an adjuvant which is selected from the group consisting of: a TLR-1 agonist, a TLR-2 agonist, TLR-3 agonist, a TLR-4 agonist, TLR-5 agonist, a TLR-6 agonist, TLR-7 agonist, a TLR-8 agonist, TLR-9 agonist, or a combination thereof.

In one embodiment of the present invention, a TLR agonist is used that is capable of causing a signaling response through TLR-1. Suitably, the TLR agonist capable of causing a signaling response through TLR-1 is selected from: Tri-acylated lipopeptides (LPs); phenol-soluble modulin; *Mycobacterium tuberculosis* LP; S-(2,3-bis(palmitoyloxy)-(2-RS)-propyl)-N-palmitoyl-(R)-Cys-(S)-Ser-(S)-Lys(4)-OH, trihydrochloride (Pam3Cys) LP which mimics the acetylated amino terminus of a bacterial lipoprotein and OspA LP from *Borrelia burgdorferi*.

In an alternative embodiment, a TLR agonist is used that is capable of causing a signaling response through TLR-2. Suitably, the TLR agonist capable of causing a signaling response through TLR-2 is one or more of a lipoprotein, a peptidoglycan, a bacterial lipopeptide from *M. tuberculosis, B. burgdorferi* or *T. pallidum*; peptidoglycans from species including *Staphylococcus aureus*; lipoteichoic acids, mannuronic acids, *Neisseria* porins, bacterial fimbriae, Yersina virulence factors, CMV virions, measles haemagglutinin, and zymosan from yeast.

In an alternative embodiment, a TLR agonist is used that is capable of causing a signaling response through TLR-3. Suitably, the TLR agonist capable of causing a signaling response through TLR-3 is double stranded RNA (dsRNA), or polyinosinic-polycytidylic acid (Poly IC), a molecular nucleic acid pattern associated with viral infection.

In an alternative embodiment, a TLR agonist is used that is capable of causing a signaling response through TLR-5. Suitably, the TLR agonist capable of causing a signaling response through TLR-5 is bacterial flagellin.

In an alternative embodiment, a TLR agonist is used that is capable of causing a signaling response through TLR-6. Suitably, the TLR agonist capable of causing a signaling response through TLR-6 is mycobacterial lipoprotein, di-acylated LP, and phenol-soluble modulin. Additional TLR6 agonists are described in WO 2003/043572.

In an alternative embodiment, a TLR agonist is used that is capable of causing a signaling response through TLR-7. Suitably, the TLR agonist capable of causing a signaling response through TLR-7 is a single stranded RNA (ssRNA), loxoribine, a guanosine analogue at positions N7 and C8, or an imidazoquinoline compound, or derivative thereof. In one embodiment, the TLR agonist is imiquimod. Further TLR7 agonists are described in WO 2002/085905.

In an alternative embodiment, a TLR agonist is used that is capable of causing a signaling response through TLR-8. Suitably, the TLR agonist capable of causing a signaling response through TLR-8 is a single stranded RNA (ssRNA), an imidazoquinoline molecule with anti-viral activity, for example resiquimod (R848); resiquimod is also capable of recognition by TLR-7. Other TLR-8 agonists which can be used include those described in WO 2004/071459.

In an alternative embodiment, a TLR agonist is used that is capable of causing a signaling response through TLR-9. In one embodiment, the TLR agonist capable of causing a signaling response through TLR-9 is HSP90. Alternatively, the TLR agonist capable of causing a signaling response through TLR-9 is bacterial or viral DNA, DNA containing unmethylated CpG nucleotides, in particular sequence contexts known as CpG motifs. CpG-containing oligonucleotides induce a predominantly Th1 response. Such oligonucleotides are well known and are described, for example, in WO 96/02555, WO 99/33488 and U.S. Pat. Nos. 6,008,200 and 5,856,462. Suitably, CpG nucleotides are CpG oligonucleotides. Suitable oligonucleotides for use in the immunogenic compositions of the present invention are CpG containing oligonucleotides, optionally containing two or more dinucleotide CpG motifs separated by at least three, suitably at least six or more nucleotides. A CpG motif is a Cytosine nucleotide followed by a Guanine nucleotide. The CpG oligonucleotides of the present invention are typically deoxynucleotides. In a specific embodiment the internucleotide in the oligonucleotide is phosphorodithioate, or suitably a phosphorothioate bond, although phosphodiester and other internucleotide bonds are within the scope of the invention. Also included within the scope of the invention are oligonucleotides with mixed internucleotide linkages. Methods for producing phosphorothioate oligonucleotides or phosphorodithioate are described in U.S. Pat. Nos. 5,666,153, 5,278,302 and WO 95/26204.

Other adjuvants that can be used in immunogenic compositions with a PreF antigens, e.g., on their own or in combination with 3D-MPL, or another adjuvant described herein, are saponins, such as QS21.

Saponins are taught in: Lacaille-Dubois, M and Wagner H. (1996. A review of the biological and pharmacological activities of saponins Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja Saponaria Molina), and fractions thereof, are described in U.S. Pat. No. 5,057,540 and "Saponins as vaccine adjuvants", Kensil, C. R., Crit. Rev Ther Drug Carrier Syst, 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1, which are incorporated herein by reference. Other saponins which have been used in systemic vaccination studies include those derived from other plant species such as Gypsophila and Saponaria (Bomford et al., Vaccine, 10(9): 572-577, 1992).

QS21 is an Hplc purified non-toxic fraction derived from the bark of Quillaja Saponaria Molina. A method for producing QS21 is disclosed in U.S. Pat. No. 5,057,540. Non-reactogenic adjuvant formulations containing QS21 are described in WO 96/33739. The aforementioned references are incorporated by reference herein. Said immunologically active saponin, such as QS21, can be used in amounts of between 1 and 50 µg, per human dose of the immunogenic composition. Advantageously QS21 is used at a level of about 25 µg, for example between 20-30 µg, suitably between 21-29 µg or between 22-28 µg or between 23-27 µg or between 24-26 µg, or 25 µg. In another embodiment, the human dose of the immunogenic composition comprises QS21 at a level of about 10 µg, for example between 5 and 15 µg, suitably between 6-14 µg, for example between 7-13 µg or between 8-12 µg or between 9-11 µg, or 10 µg. In a further embodiment, the human dose of the immunogenic composition comprises QS21 at a level of about 5 µg, for example between 1-9 µg, or between 2-8 µg or suitably between 3-7 µg or 4-6 µg, or 5 µg. Such formulations comprising QS21 and cholesterol have been shown to be successful Th1 stimulating adjuvants when formulated together with an antigen. Thus, for example, PreF polypeptides can favorably be employed in immunogenic compositions with an adjuvant comprising a combination of QS21 and cholesterol.

Optionally, the adjuvant can also include mineral salts such as an aluminium or calcium salts, in particular aluminium hydroxide, aluminium phosphate and calcium phosphate. For example, an adjuvant containing 3D-MPL in combination with an aluminium salt (e.g., aluminium hydroxide or "alum") is suitable for formulation in an immunogenic composition containing a PreF antigen for administration to a human subject.

Another class of suitable Th1 biasing adjuvants for use in formulations with PreF antigens includes OMP-based immunostimulatory compositions. OMP-based immunostimulatory compositions are particularly suitable as mucosal adjuvants, e.g., for intranasal administration. OMP-based immunostimulatory compositions are a genus of preparations of outer membrane proteins (OMPs, including some porins) from Gram-negative bacteria, such as, but not limited to, Neisseria species (see, e.g., Lowell et al., J. Exp. Med. 167: 658, 1988; Lowell et al., Science 240:800, 1988; Lynch et al., Biophys. J. 45:104, 1984; Lowell, in "New Generation Vaccines" 2nd ed., Marcel Dekker, Inc., New York, Basil, Hong Kong, page 193, 1997; U.S. Pat. No. 5,726,292; U.S. Pat. No. 4,707,543), which are useful as a carrier or in compositions for immunogens, such as bacterial or viral antigens. Some OMP-based immunostimulatory compositions can be referred to as "Proteosomes," which are hydrophobic and safe for human use. Proteosomes have the capability to auto-assemble into vesicle or vesicle-like OMP clusters of about 20 nm to about 800 nm, and to noncovalently incorporate, coordinate, associate (e.g., electrostatically or hydrophobically), or otherwise cooperate with protein antigens (Ags), particularly antigens that have a hydrophobic moiety. Any preparation method that results in the outer membrane protein component in vesicular or vesicle-like form, including multi-molecular membranous structures or molten globular-like OMP compositions of one or more OMPs, is included within the definition of Proteosome. Proteosomes can be prepared, for example, as described in the art (see, e.g., U.S. Pat. No. 5,726,292 or U.S. Pat. No. 5,985,284). Proteosomes can also contain an endogenous lipopolysaccharide or lipooligosaccharide (LPS or LOS, respectively) originating from the bacteria used to produce the OMP porins (e.g., Neisseria species), which generally will be less than 2% of the total OMP preparation.

Proteosomes are composed primarily of chemically extracted outer membrane proteins (OMPs) from Neisseria menigitidis (mostly porins A and B as well as class 4 OMP), maintained in solution by detergent (Lowell G H. Proteosomes for Improved Nasal, Oral, or Injectable Vaccines. In: Levine M M, Woodrow G C, Kaper J B, Cobon G S, eds, New Generation Vaccines. New York: Marcel Dekker, Inc. 1997; 193-206). Proteosomes can be formulated with a variety of antigens such as purified or recombinant proteins derived from viral sources, including the PreF polypeptides disclosed herein, e.g., by diafiltration or traditional dialysis processes. The gradual removal of detergent allows the formation of particulate hydrophobic complexes of approximately 100-200 nm in diameter (Lowell G H. Proteosomes for Improved Nasal, Oral, or Injectable Vaccines. In: Levine M M, Woodrow G C, Kaper J B, Cobon G S, eds, New Generation Vaccines. New York: Marcel Dekker, Inc. 1997; 193-206).

"Proteosome: LPS or Protollin" as used herein refers to preparations of proteosomes admixed, e.g., by the exogenous addition, with at least one kind of lipo-polysaccharide to provide an OMP-LPS composition (which can function as an immunostimulatory composition). Thus, the OMP-LPS composition can be comprised of two of the basic components of Protollin, which include (1) an outer membrane protein preparation of Proteosomes (e.g., Projuvant) prepared from Gram-negative bacteria, such as *Neisseria meningitidis*, and (2) a preparation of one or more liposaccharides. A lipo-oligosaccharide can be endogenous (e.g., naturally contained with the OMP Proteosome preparation), can be admixed or combined with an OMP preparation from an exogenously prepared lipo-oligosaccharide (e.g., prepared from a different culture or microorganism than the OMP preparation), or can be a combination thereof. Such exogenously added LPS can be from the same Gram-negative bacterium from which the OMP preparation was made or from a different Gram-negative bacterium. Protollin should also be understood to optionally include lipids, glycolipids, glycoproteins, small molecules, or the like, and combinations thereof. The Protollin can be prepared, for example, as described in U.S. Patent Application Publication No. 2003/0044425.

Combinations of different adjuvants, such as those mentioned hereinabove, can also be used in compositions with PreF antigens. For example, as already noted, QS21 can be formulated together with 3D-MPL. The ratio of QS21:3D-MPL will typically be in the order of 1:10 to 10:1; such as 1:5 to 5:1, and often substantially 1:1. Typically, the ratio is in the range of 2.5:1 to 1:1 3D-MPL: QS21. Another combination adjuvant formulation includes 3D-MPL and an aluminium salt, such as aluminium hydroxide. When formulated in combination, this combination can enhance an antigen-specific Th1 immune response.

In some instances, the adjuvant formulation includes an oil-in-water emulsion, or a mineral salt such as a calcium or aluminium salt, for example calcium phosphate, aluminium phosphate or aluminium hydroxide.

In some embodiments, the adjuvant includes an oil and water emulsion, e.g., an oil-in-water emulasion. One example of an oil-in-water emulsion comprises a metabolisable oil, such as squalene, a tocol such as a tocopherol, e.g., alpha-tocopherol, and a surfactant, such as sorbitan trioleate (Span 85™) or polyoxyethylene sorbitan monooleate (Tween 80™), in an aqueous carrier. In certain embodiments, the oil-in-water emulsion does not contain any additional immunostimulants(s), (in particular it does not contain a non-toxic lipid A derivative, such as 3D-MPL, or a saponin, such as QS21). The aqueous carrier can be, for example, phosphate buffered saline. Additionally the oil-in-water emulsion can contain span 85 and/or lecithin and/or tricaprylin.

In another embodiment of the invention there is provided a vaccine composition comprising an antigen or antigen composition and an adjuvant composition comprising an oil-in-water emulsion and optionally one or more further immunostimulants, wherein said oil-in-water emulsion comprises 0.5-10 mg metabolisable oil (suitably squalene), 0.5-11 mg tocol (suitably a tocopherol, such as alpha-tocopherol) and 0.4-4 mg emulsifying agent.

In one specific embodiment, the adjuvant formulation includes 3D-MPL prepared in the form of an emulsion, such as an oil-in-water emulsion. In some cases, the emulsion has a small particle size of less than 0.2 μm in diameter, as disclosed in WO 94/21292. For example, the particles of 3D-MPL can be small enough to be sterile filtered through a 0.22 micron membrane (as described in European Patent number 0 689 454). Alternatively, the 3D-MPL can be prepared in a liposomal formulation. Optionally, the adjuvant containing 3D-MPL (or a derivative thereof) also includes an additional immunostimulatory component.

The adjuvant is selected to be safe and effective in the population to which the immunogenic composition is administered. For adult and elderly populations, the formulations typically include more of an adjuvant component than is typically found in an infant formulation. In particular formulations using an oil-in-water emulsion, such an emulsion can include additional components, for example, such as cholesterol, squalene, alpha tocopherol, and/or a detergent, such as tween 80 or span85. In exemplary formulations, such components can be present in the following amounts: from about 1-50 mg cholesterol, from 2 to 10% squalene, from 2 to 10% alpha tocopherol and from 0.3 to 3% tween 80. Typically, the ratio of squalene:alpha tocopherol is equal to or less than 1 as this provides a more stable emulsion. In some cases, the formulation can also contain a stabilizer.

For example, when an immunogenic composition with a PreF polypeptide antigen is formulated for administration to an infant, the dosage of adjuvant is determined to be effective and relatively non-reactogenic in an infant subject. Generally, the dosage of adjuvant in an infant formulation is lower than that used in formulations designed for administration to adult (e.g., adults aged 65 or older). Generally, the dosage of adjuvant in an infant formulation is lower (for example, the dose may be a fraction of the dose provided in a formulation to be administered to adults) than that used in formulations designed for administration to adult (e.g., adults aged 65 or older). For example, the amount of 3D-MPL is typically in the range of 1 μg-200 μg, such as 10-100 μg, or 10 μg-50 μg per dose. An infant dose is typically at the lower end of this range, e.g., from about 1 μg to about 50 μg, such as from about 2 μg, or about 5 μg, or about 10 μg, to about 25 μg, or to about 50 μg. Typically, where QS21 is used in the formulation, the ranges are comparable (and according to the ratios indicated above). In the case of an oil and water emulsion (e.g., an oil-in-water emulsion), the dose of adjuvant provided to a child or infant can be a fraction of the dose administered to an adult subject. Where alum is present, e.g., in combination with 3D-MPL, the amount is typically between about 100 μg and 1 mg, such as from about 100 μg, or about 200 μg to about 750 μg, such as about 500 μg per dose.

An immunogenic composition typically contains an immunoprotective quantity (or a fractional dose thereof) of the antigen and can be prepared by conventional techniques. Preparation of Immunogenic Compositions, Including Those for Administration to Human Subjects, is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

Typically, the amount of protein in each dose of the immunogenic composition is selected as an amount which induces an immunoprotective response without significant, adverse side effects in the typical subject. Immunoprotective in this context does not necessarily mean completely protective against infection; it means protection against symptoms or disease, especially severe disease associated with the virus. The amount of antigen can vary depending upon which specific immunogen is employed. Generally, it is expected that each human dose will comprise 1-1000 µg of protein, such as from about 1 µg to about 100 µg, for example, from about 1 µg to about 50 µg, such as about 1 µg, about 2 µg, about 5 µg, about 10 µg, about 15 µg, about 20 µg, about 25 µg, about 30 µg, about 40 µg, or about 50 µg. The amount utilized in an immunogenic composition is selected based on the subject population (e.g., infant or elderly). An optimal amount for a particular composition can be ascertained by standard studies involving observation of antibody titres and other responses in subjects. Following an initial vaccination, subjects can receive a boost in about 4 weeks.

It should be noted that regardless of the adjuvant selected, the concentration in the final formulation is calculated to be safe and effective in the target population. For example, immunogenic compositions for eliciting an immune response against paramyxoviruses, e.g., RSV, hMPV and PIV, in humans are favorably administered to infants (e.g., infants between birth and 1 year, such as between 0 and 6 months, at the age of initial dose). Immunogenic compositions for eliciting an immune response against paramyxoviruses, e.g., RSV, hMPV and PIV, are also favorably administered to elderly humans (e.g., alone or in a combination with an influenza antigen and/or antigens of other pathogens associated with COPD). It will be appreciated that the choice of adjuvant can be different in these different applications, and the optimal adjuvant and concentration for each situation can be determined empirically by those of skill in the art.

Accordingly, the use of PreF antigens or nucleic acids that encode them in the preparation of a medicament for treating (either therapeutically following or prophylactically prior to) exposure to or infection by two or more of hMPV, PIV and RSV is also a feature of this disclosure. Likewise, methods for eliciting an immune response against hMPV, PIV and/or RSV in a subject are a feature of this disclosure. Such methods include administering an immunologically effective amount of a composition comprising a PreF antigen to a subject, such as a human subject. Commonly, the composition includes an adjuvant that elicits a Th1 biased immune response. The composition is formulated to elicit an immune response specific for hMPV, PIV and/or RSV without enhancing viral disease following contact with any one of these pathogens. That is, the composition is formulated to and results in a Th1 biased immune response that reduces or prevents infection with hMPV, PIV and/or RSV and/or reduces or prevents a pathological response following infection with these paramyxoviruses. Although the composition can be administered by a variety of different routes, most commonly, the immunogenic compositions are delivered by an intramuscular or intranasal route of administration.

An immunogenic composition typically contains an immunoprotective quantity (or a fractional dose thereof) of the antigen and can be prepared by conventional techniques. Preparation of Immunogenic Compositions, Including Those for Administration to Human Subjects, is generally described in Pharmaceutical Biotechnology, Vol. 61 Vaccine Design— the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

Typically, the amount of protein in each dose of the immunogenic composition is selected as an amount which induces an immunoprotective response without significant, adverse side effects in the typical subject. Immunoprotective in this context does not necessarily mean completely protective against infection; it means protection against symptoms or disease, especially severe disease associated with the virus. The amount of antigen can vary depending upon which specific immunogen is employed. Generally, it is expected that each human dose will comprise 1 1000 µg of protein, such as from about 1 µg to about 100 µg, for example, from about 1 µg to about 50 µg, such as about 1 µg, about 2 µg, about 5 µg, about 10 µg, about 15 µg, about 20 µg, about 25 µg, about 30 µg, about 40 µg, or about 50 µg. The amount utilized in an immunogenic composition is selected based on the subject population (e.g., infant or elderly). An optimal amount for a particular composition can be ascertained by standard studies involving observation of antibody titres and other responses in subjects. Following an initial vaccination, subjects can receive a boost in about 4-12 weeks. For example, when administering an immunogenic composition containing a PreF antigen to an infant subject, the initial and subsequent inoculations can be administered to coincide with other vaccines administered during this period.

The following examples are provided to illustrate certain particular features and/or embodiments. These examples should not be construed to limit the invention to the particular features or embodiments described.

EXAMPLES

Example 1

Exemplary PreF Antigens

Respiratory Syncytial Virus

Exemplary paramyxovirus PreF antigens were produced based on the RSV F protein as disclosed in WO2009/079796 (US 2010/0291147), which is incorporated herein for all purposes. Modifications were made in the RSV F protein in order to stabilize the protein in its prefusion conformation, based on the prediction that an immune response generated to the prefusion conformation of F would preferentially include antibodies that would prevent binding, conformation shifting and/or other events involved in membrane fusion, thereby increasing the efficacy of the protective response.

FIGS. 1A and B schematically illustrate features of RSV F0 and exemplary PreF recombinant antigens. FIG. 1A is a representation of the RSV F0 protein. F0 is a pre-protein consisting of 574 amino acids. The F0 pre-protein is proteolytically processed and glycosylated following translation. A signal peptide, which is later removed by a signal peptidase, targets translation of the F0 pre-protein to the reticulum endoplasmic (RE). Nascent peptide in the RE is then N-glycosylated at multiple sites (represented by triangles). Furin cleavage of F0 generates F2 and F1 peptide domains, which are folded and assembled together as a trimer of F2-F1 heterodimers (that is, 3 times F2-F1). In its native state, the F protein is anchored to the membrane by a transmembrane helix in the C-terminal region. Additional features of the F0 polypeptide include, 15 Cysteine residues, 4 characterized neutralizing epitopes, 2 coiled-coil regions, and a lipidation motif. FIG. 1B illustrates features of exemplary PreF antigens. To construct the PreF antigen, the F0 polypeptide was modified to stabilize the prefusion conformation of the F protein, thereby retaining the predominant immunogenic epitopes of the F protein as presented by the RSV virus prior to binding to and fusion with host cells. The following stabilizing mutations were introduced into the PreF antigen relative to the F0 polypeptide. First, a stabilizing coiled-coil domain was placed at the C-terminal end of the extracellular domain of the F0 polypeptide, replacing the membrane anchoring domain of F0. Second, the pep27 peptide (situated between the F2 and F1 domains in the native protein) was removed. Third, both furin motifs were eliminated. In alternative embodiments (designated PreF_V1 and PreF_V2), an immunologically active portion (e.g., amino acids 149-229) of the RSV G protein was added to the C-terminal domain. The sequence of the exemplary RSV PreF antigen is represented by SEQ ID NO:10.

Figure 6A:
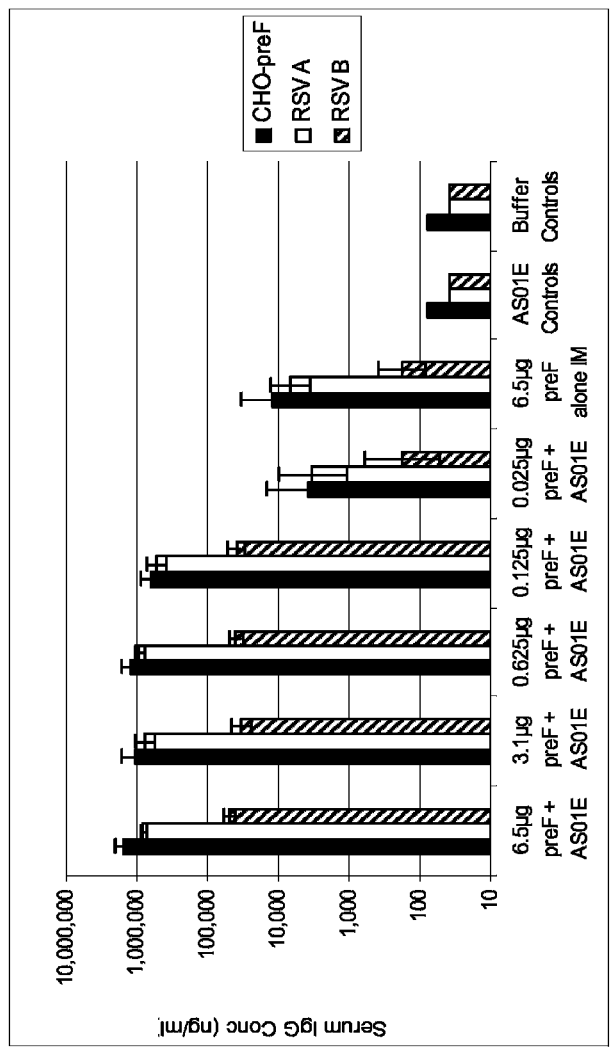
FIGS. 6A and B are bar graphs illustrating titers of IgG and neutralizing antibodies specific for RSV elicited by PreF antigen.

As disclosed in detail in WO2009/079796 (US 2010/0291147)$_7$, the exemplary PreF antigen was shown to elicit a robust immune response specific for RSV. FIGS. 6A and B illustrate characteristic IgG and neutralizing antibody responses. FIG. 7 illustrates protection against RSV infection conferred by administration of the exemplary PreF antigen. Human Metapneumovirus (hMPV) and Parainfluenza Virus 3 (PIV-3)

Additional PreF antigens were produced corresponding to the hMPV and PIV-3 fusion proteins. The sequences of these PreF polypeptides are represented by SEQ ID NOs:12 and 14, respectively. As was shown for RSV PreF antigen, the hMPV and PIV-3 PreF polypeptides self assemble into trimers in solution.

To confirm immunogenicity of the hMPV and PIV-3 PreF polypeptides, and demonstrate their suitability as antigens for use in a combination vaccine for preventing infection by paramyxoviruses, mice were immunized with immunogenic compositions comprising one or more PreF polypeptides alone and in double and triple combination, as indicated in Table 1.

TABLE 1

Immunization Protocol: RSV, hMPV, PIV-3 combination compositions

| Group | Immunogen | Dose preF (µg) | Dose (µg/mL) | Adjuvant | Volume (µL) |
|---|---|---|---|---|---|
| 1 | PreF from RSV, hMPV and PIV-3 | 3 × 2 | 120 | AS03B | 50 |
| 2 | PreF from RSV and hMPV | 2 × 2 | 80 | AS03B | 50 |
| 3 | PreF from RSV and PIV-3 | 2 × 2 | 80 | AS03B | 50 |
| 4 | PreF from RSV | 2 | 40 | AS03B | 50 |
| 5 | PreF from hMPV | 2 | 40 | AS03B | 50 |
| 6 | PreF from PIV-3 | 2 | 40 | AS03B | 50 |
| 7 | None | — | — | AS03B | 50 |

Figure 8A:
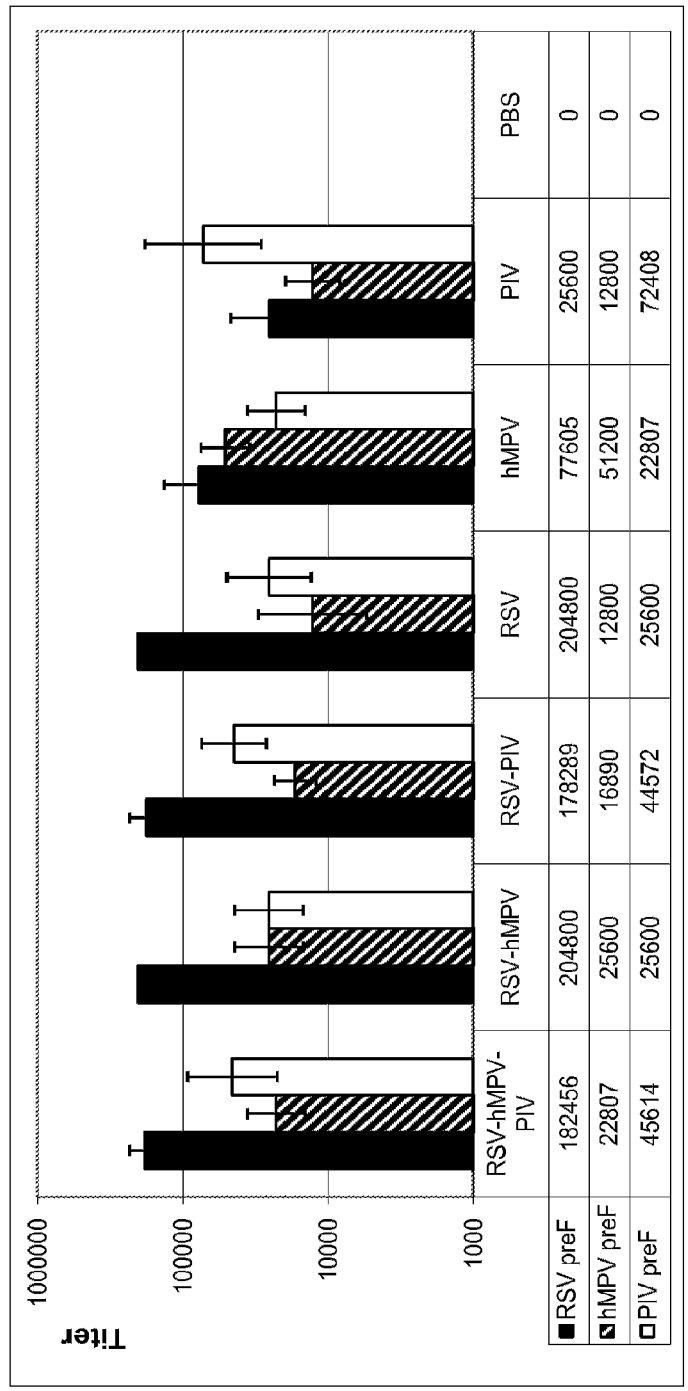
FIGS. 8A and B are bar graphs illustrating titers of IgG and neutralizing antibodies specific for components of immunogenic compositions comprising combinations of paramyxovirus F protein antigens.

Antigen-specific IgG antibody titers were determined on individual serum samples by ELISA. Briefly, 3 series of 96-well plates were each coated with one preF from RSV, hMPV or PIV (0.5 µg) protein and incubated overnight at 4° C. Serum samples were serially diluted in blocking buffer starting at 1:200 and incubated for 2 h at room temperature. Bound antibody was detected with horseradish peroxidase (HRP)-conjugated anti-mouse IgG (Sigma, ON). 3,3A,5,5A-tetramethylbenzidine (TMB, BD Opt EIATM, BD Biosciences, ON) was used as the substrate for HRP. 50 µl of 1M H2SO4 was added to each well to stop the reaction. Absorbance values for each well were detected at 450 nm with a Molecular Devices microplate reader (Molecular Devices, USA). Results are expressed as geometric mean titers (GMT+/−95% CL). Illustrative results are shown in FIG. 8A.

All three PreF antigens, alone or in double and triple combination elicited significant IgG antibody titers as detected by ELISA.

The presence of high titers of neutralizing antibodies has been shown to be a correlate of protection against paramyxovirus infection. To demonstrate that the PreF polypeptides are capable of eliciting a protective immune response, sera from trivalent, bivalent and monovalent—AS03 immunized mice were evaluated for neutralization potential against the viruses. The assay for detecting neutralizing antibodies was based on the $TCID_{50}$ method Sera from individual immunized animals were serially diluted from a starting dilution of 1:16 in medium in 96-well plates (20 µl/well). Control wells contained medium only or virus specific antibody. Titration of virus was performed prior to the neutralization assay. Standardization between the different viruses was based on infectivity on Vero cells. 20 ul/well of virus stock (titers below) was added to the plates.
RSV→$2.67 \times 10^7$ $TCID_{50}$/ml
hMPV→$2.81 \times 10^7$ $TCID_{50}$/ml
PIV-3→$2.11 \times 10^9$ $TCID_{50}$/ml The plates were incubated for 20 minutes at 33° C. and the mixture was transferred to 96-well flat-bottomed plates previously seeded with $1 \times 10^5$ cells/mL Vero cells. After 4 days at 33° C. (5% $CO_2$), supernatants were removed; plates were washed with PBS and adhering cells fixed with 1% paraformaldehyde in PBS for 1 hour. Infection was monitored by indirect immunofluorescence (RSV; hMPV) or cytopathic effect (PIV-3).

The 50% tissue culture infective dose (TCID50) calculations were performed using the Spearman-Karber (SK) method and percentages of NI calculated as follow:

$$\frac{\text{Neut titer (0 ug/ml inhibitor)} - \text{Neut titer (25 µg/ml inhibitor)}}{\text{Neut titer (0 µg/ml inhibitor)}} \times 100$$

As shown in FIG. 8B, all of the PreF antigens, whether alone or in combination, elicited specific neutralizing antibodies capable of inhibiting viral replication.

We claim:

1. An immunogenic composition comprising at least two F protein antigens of different paramyxoviruses selected from the group of: human metapneumovirus (hMPV), parainfluenza virus 3 (PIV-3), and respiratory syncytial virus (RSV), wherein the at least two paramyxovirus F protein antigens each comprise a recombinant F protein polypeptide comprising an $F_2$ domain and an $F_1$ domain of a paramyxovirus F protein polypeptide, wherein the F protein polypeptide of hMPV and PIV-3 comprise a deletion of a furin cleavage site and a heterologous coiled-coil trimerization domain and wherein the F protein polypeptide of RSV lacks a transmembrane domain and comprises a deletion of two furin cleavage sites, a deletion of pep27, and a heterologous coiled-coil trimerization domain.

2. The immunogenic composition of claim 1, wherein the heterologous multimerization domain is positioned C-terminal to the $F_1$ domain.

3. The immunogenic composition of claim 1, wherein at least one of the F protein polypeptides comprises an F2 domain and an F1 domain with no intervening furin cleavage site.

4. The immunogenic composition of claim 1, wherein at least one of the F protein polypeptides comprises an intact fusion peptide between the F2 domain and the F1 domain.

5. The immunogenic composition of claim 1, wherein at least one of the F protein polypeptides comprises at least one modification selected from:
   (a) a deletion of at least one enzymatic cleavage site other than a furin cleavage site;
   (b) at least one substitution or addition of a hydrophilic amino acid in a hydrophobic domain of the F protein extracellular domain; and
   (c) an amino acid substitution that alters glycosylation.

6. The immunogenic composition of claim 1 wherein the at least two paramyxovirus F protein antigens comprise a human respiratory syncytial virus (RSV) F protein antigen and at least one of a human metapneumovirus (hMPV) F protein antigen and a parainfluenza virus 3 (PIV-3) F protein antigen.

7. The immunogenic composition of claim 1 wherein the at least two paramyxovirus F protein antigens comprise a human metapneumovirus (hMPV) F protein antigen and a parainfluenza virus 3 (PIV-3) F protein antigen.

8. The immunogenic composition of claim 1 wherein at least one of the F protein polypeptides comprises a heterologous trimerization domain comprising a coiled-coil domain.

9. The immunogenic composition of claim 1 wherein at least one of the F protein polypeptides comprises at least one amino acid addition, deletion or substitution that eliminates a furin cleavage site present in a naturally occurring F protein precursor ($F_o$).

10. The immunogenic composition of claim 1, wherein at least one of the F protein polypeptides further comprises at least one modification that alters glycosylation.

11. The immunogenic composition of claim 1, wherein one or more of the at least two paramyxovirus F protein antigens are selected from the group of:
   a) an RSV F protein polypeptide comprising or consisting of SEQ ID NO:10, an hMPV F protein polypeptide comprising or consisting of SEQ ID NO:12, and a PIV-3 F protein polypeptide comprising or consisting of SEQ ID NO:14; and
   b) a PreF polypeptide with at least 89% sequence identity to SEQ ID NO:10; a PreF polypeptide with at least 94% sequence identity to SEQ ID NO:12; and a PreF polypeptide with at least 95% sequence identity to SEQ ID NO:14.

12. The immunogenic composition of claim 1 wherein at least one of the F protein polypeptides assembles into a multimer of polypeptides.

13. The immunogenic composition of claim 12, wherein at least one of the F protein polypeptides assembles into-a trimer of polypeptides.

14. The immunogenic composition of claim 1, further comprising a carrier or excipient.

15. The immunogenic composition of claim 1 further comprising an adjuvant.

16. The immunogenic composition of claim 1 wherein the immunogenic composition reduces infection with two or more of hMPV, PIV-3 and RSV.

17. The immunogenic composition of claim 1, wherein the immunogenic composition reduces or prevents a pathological symptom or disease following infection with at least two of hMPV, PIV-3 RSV.

18. A method for eliciting an immune response against one or more of hMPV, PIV-3 and RSV, the method comprising:
   administering to a subject the immunogenic composition of claim 1.

19. The method of claim 18, wherein the immune response reduces infection with one or more of hMPV, PIV-3 and RSV.

20. The method of claim 18, wherein the subject is a human subject.

* * * * *

SEQUENCE LISTING

```
<160> NUMBER OF SEQ ID NOS: 15

<210> SEQ ID NO 1
<211> LENGTH: 1697
<212> TYPE: DNA
<213> ORGANISM: respiratory syncytial virus

<400> SEQUENCE: 1
atggagttgc taatcctcaa agcaaatgca attaccacaa tcctcactgc agtcacattt      60
gttttgcttc tggtcaaaac atcactgaag aattttatca atcaacatgc agtgcagtag     120
```

-continued

```
caaaggctat cttagtgctc tgagaactgg ttggtatacc agtgttataa ctatagatta      180
agtaatatca aggaaaataa gtgtaatgga acagatgcta aggtaaaatt gataaacaag      240
aattagataa atataaaaat gctgtaacag aattgcagtt gctcatgcaa agcacccagc      300
aacaaacaat cgagccagaa gagaactacc aaggtttatg aattatacac tcaaaatgcc      360
aaaaaaacca atgtaacatt aagcaagaaa aggaaaagaa gatttcttgg tttttgttag      420
gtgttggatc tgcaatcgcc agtggcgttg ctgtatctaa ggtcctgcac ctgaagggga      480
agtgaacaag atcaaagtg ctctactatc acaaacaag gctgtagtca gttatcaaat       540
ggagttagtg tcttaaccag caaagtgtta gaccctcaaaa actatataga aaacaattgt     600
tacctattgt gaacaagcaa agctgcagca tatcaaatat agcaactgta tagagttcca     660 acaaagaac aacagactac tagagattac cagggaattt agtgttaagc aggtgtaact       720
acacctgtaa gcacttacat gttaactaat agtgaattat tgtcattatc aatgatatgc     780
ctataacaaa tgatcagaaa aagtaatgt ccaacaatgt tcaaatgtta gacagcaaag       840
ttactctatc atgtccataa taaaagagga agtcttagca tatgtgtaca attaccacta     900
tatggtgtta tagatacacc ctgttggaaa ctacacacat cccctatgt acaaccaaca      960 caaagaagg gtccaacatc tgtttaacaa gaactgacag aggtggtact gtgacaatgc     1020
aggatcagta tctttcttcc cacaagctga aacatgtaaa gtcaatcaaa tcgagtattt    1080
tgtgacacaa tgaacagttt aacattacca agtgaagtaa actctgcaat gttgacatat    1140
tcaaccccaa atatgattgt aaaattatga cttcaaaaac gatgtaagca gctccgttat    1200
cacatctcta ggagccattg tgtcatgcta tggcaaaaca aatgtacagc atccaataaa    1260
aatcgtggaa tcataaagac attttctaac gggtgcgata tgtatcaaat aaaggggtgg    1320
acactgtgtc tgtaggtaac acattatatt atgtaaaaag caagaaggta aaagtctcta    1380
tgtaaaaggt gaaccaataa taatttcta tgacccttag tattcccctc tgatgaattt      1440
gatgcatcaa tatctcaagt caacgagaag attaacagag cctagcattt attcgtaaat    1500
ccgatgaatt attacataat gtaaatgctg gtaatccacc ataaatatca tgataactac    1560
tataattata gtgattatag taatattgtt atcttaattg ctgttggact gctcttatac    1620
tgtaaggcca gaagcacacc agtcacacta agaaagatca actgagtggt ataataata    1680 ttgcatttag taactaa                                                   1697
```

<210> SEQ ID NO 2
<211> LENGTH: 574
<212> TYPE: PRT
<213> ORGANISM: respiratory syncytial virus

<400> SEQUENCE: 2

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
```

```
            85                  90                  95
Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
            130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Ala Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510
```

-continued

```
Leu His Asn Val Asn Ala Gly Lys Ser Thr Ile Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 3
<211> LENGTH: 897
<212> TYPE: DNA
<213> ORGANISM: respiratory syncytial virus

<400> SEQUENCE: 3
atgtccaaaa acaaggacca acgcaccgct aagacactag aaaagacctg ggacactctc      60
aatcatttat tattcatatc atcgggctta tataagttaa atcttaaatc tatagcacaa     120
atcacattat ccattctggc aatgataatc tcaacttcac ttataattac agccatcata     180
ttcatagcct cggcaaacca caaagtcaca ctaacaactg caatcataca agatgcaaca     240
agccagatca agaacacaac cccaacatac ctcactcagg atcctcagct tggaatcagc     300
ttctccaatc tgtctgaaat tacatcacaa accaccacca tactagcttc aacaacacca     360
ggagtcaagt caaacctgca acccacaaca gtcaagacta aaaacacaac aacaacccaa     420
acacaaccca gcaagcccac tacaaaacaa cgccaaaaca aaccaccaaa caaacccaat     480
aatgattttc acttcgaagt gtttaacttt gtaccctgca gcatatgcag caacaatcca     540
acctgctggg ctatctgcaa aagaatacca aacaaaaaac caggaaagaa aaccaccacc     600
aagcctacaa aaaaaccaac cttcaagaca accaaaaaag atctcaaacc tcaaaccact     660
aaaccaaagg aagtacccac caccaagccc acagaagagc caaccatcaa caccaccaaa     720
acaaacatca caactacact gctcaccaac aacaccacag gaaatccaaa actcacaagt     780
caaatggaaa ccttccactc aacctcctcc gaaggcaatc taagcccttc tcaagtctcc     840
acaacatccg agcacccatc acaaccctca tctccaccca acacaacacg ccagtag        897

<210> SEQ ID NO 4
<211> LENGTH: 298
<212> TYPE: PRT
<213> ORGANISM: respiratory syncytial virus

<400> SEQUENCE: 4

Met Ser Lys Asn Lys Asp Gln Arg Thr Ala Lys Thr Leu Glu Lys Thr
1               5                   10                  15

Trp Asp Thr Leu Asn His Leu Leu Phe Ile Ser Ser Gly Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Thr Ala Ile Ile Phe Ile Ala Ser
    50                  55                  60

Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asp Pro Gln
                85                  90                  95

Leu Gly Ile Ser Phe Ser Asn Leu Ser Glu Ile Thr Ser Gln Thr Thr
            100                 105                 110
```

Thr Ile Leu Ala Ser Thr Thr Pro Gly Val Lys Ser Asn Leu Gln Pro
            115                 120                 125

Thr Thr Val Lys Thr Lys Asn Thr Thr Thr Thr Gln Thr Gln Pro Ser
        130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Phe
        195                 200                 205

Lys Thr Thr Lys Lys Asp Leu Lys Pro Gln Thr Thr Lys Pro Lys Glu
    210                 215                 220

Val Pro Thr Thr Lys Pro Thr Glu Glu Pro Thr Ile Asn Thr Thr Lys
225                 230                 235                 240

Thr Asn Ile Thr Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
            260                 265                 270

Asn Leu Ser Pro Ser Gln Val Ser Thr Thr Ser Glu His Pro Ser Gln
        275                 280                 285

Pro Ser Ser Pro Pro Asn Thr Thr Arg Gln
    290                 295

<210> SEQ ID NO 5
<211> LENGTH: 1620
<212> TYPE: DNA
<213> ORGANISM: human metapneumovirus

<400> SEQUENCE: 5

| | |
|---|---|
| atgtcttgga aagtggtgat catttttttca ttgctaataa cacctcaaca cggtcttaaa | 60 |
| gagagctacc tagaagaatc atgtagcact ataactgagg gatatcttag tgttctgagg | 120 |
| acaggttggt ataccaacgt ttttacatta gaggtgggtg atgtagaaaa ccttacatgt | 180 |
| tctgatggac ctagcctaat aaaaacagaa ttagatctga ccaaaagtgc actaagagag | 240 |
| ctcaaaacag tctctgctga ccaattggca agagaggaac aaattgagaa tcccagacaa | 300 |
| tctaggtttg ttctaggagc aatagcactc ggtgttgcaa cagcagctgc agtcacagca | 360 |
| ggtgttgcaa ttgccaaaac catccggctt gagagtgaag tcacagcaat taagaatgcc | 420 |
| ctcaaaacga ccaatgaagc agtatctaca ttggggaatg gagttcgagt gttggcaact | 480 |
| gcagtgagag agctgaaaga ctttgtgagc aagaatttaa ctcgtgcaat caacaaaaac | 540 |
| aagtgcgaca ttgatgacct aaaaatggcc gttagcttca gtcaattcaa cagaaggttt | 600 |
| ctaaatgttg tgcggcaatt ttcagacaat gctggaataa caccagcaat atctttggac | 660 |
| ttaatgacag atgctgaact agccagggcc gtttctaaca tgccgacatc tgcaggacaa | 720 |
| ataaaattga tgttggagaa ccgtgcgatg gtgcgaagaa aggggttcgg aatcctgata | 780 |
| ggggtctacg ggagctccgt aatttacatg gtgcagctgc caatctttgg cgttatagac | 840 |
| acgccttgct ggatagtaaa agcagcccct tcttgttccg aaaaaaaggg aaactatgct | 900 |
| tgcctcttaa gagaagacca agggtggtat tgtcagaatg cagggtcaac tgtttactac | 960 |
| ccaaatgaga aagactgtga acaagaggga gaccatgtct ttgcgacaca agcagcggga | 1020 |

-continued

```
attaatgttg ctgagcaatc aaaggagtgc aacatcaaca tatccactac aaattaccca    1080
tgcaaagtca gcacaggaag acatcctatc agtatggttg cactgtctcc tcttggggct    1140
ctggttgctt gctacaaagg agtaagctgt tccattggca gcaacagagt agggatcatc    1200
aagcagctga acaagggttg ctcctatata accaaccaag atgcagacac agtgacaata    1260
gacaacactg tatatcagct aagcaaagtt gagggtgaac agcatgttat aaaaggcaga    1320
ccagtgtcaa gcagctttga tccaatcaag tttcctgaag atcaattcaa tgttgcactt    1380
gaccaagttt ttgagaacat tgaaaacagc caggccttgg tagatcaatc aaacagaatc    1440
ctaagcagtg cagagaaagg aatactggc ttcatcattg taataattct aattgctgtc    1500
cttggctcta gcatgatcct agtgagcatc ttcattataa tcaagaaaac aaagaaacca    1560
acgggagcac ctccagagct gagtggtgtc acaaacaatg gcttcatacc acataattag    1620
```

<210> SEQ ID NO 6
<211> LENGTH: 539
<212> TYPE: PRT
<213> ORGANISM: human metapneumovirus

<400> SEQUENCE: 6

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Thr Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270
```

-continued

```
Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535
```

<210> SEQ ID NO 7
<211> LENGTH: 1620
<212> TYPE: DNA
<213> ORGANISM: parainfluenza virus 3

<400> SEQUENCE: 7

```
atgccaacct caatactgct aattattaca accatgatta tggcatcttt ctgccaaata      60
gatatcacaa aactacagca tgtaggtgta ttggttaaca gtcccaaagg gatgaagata     120
tcacaaaact ttgaaacaag atatctaatt ttgagcctca taccaaaaat agaagattct     180
aactcttgtg gtgaccaaca gatcaagcaa tacaagaggt tattggatag actgatcatt     240
cctttatatg atggattaag attacagaag gatgtgatag tgtccaatca agaatccaat     300
gaaaacactg accccagaac aaaacgattc tttggagggg taattggaac tattgctctg     360
ggagtggcaa cctcagcaca aattacagcg gcagttgctc tggttgaagc caagcaggca     420
agatcagaca ttgaaaaact caaggaagca atcagggaca caaacaaagc agtgcagtca     480
gtccagagct ccataggaaa tttgatagta gcaattaaat cggtccagga ttatgtcaac     540
aaagaaatcg tgccatcaat tgcgagatta ggttgtgaag cagcaggact tcagttagga     600
```

```
attgcattaa cacagcatta ctcagaatta acaaacatat tcggtgataa cataggatcg    660
ttacaagaaa aagggataaa attacaaggt atagcatcat tataccgcac aaatatcaca    720
gagatattca caacatcaac agttgataaa tatgatattt atgatctatt atttacagaa    780
tcaataaagg tgagagttat agatgttgac ttgaatgatt actcaatcac cctccaagtc    840
agactccctt tattaactag actgctgaac acccagattt acaaagtaga ttccatatca    900
tacaacatcc aaaacagaga atggtatatc cctcttccca gccacatcat gacaaaaggg    960
gcatttctag gtggagcaga tgtcaaagaa tgtatagaag cattcagcag ttatatatgc   1020
ccttctgatc caggatttgt actaaaccat gaaatggaga gctgtttatc aggaaacata   1080
tcccaatgtc caagaaccgt ggtcacatca gacattgttc caagatatgc atttgtcaat   1140
ggaggagtgg ttgcaaattg tataacaacc acatgtacat gcaacggtat cggcaataga   1200
atcaatcaac cacctgatca aggagtaaaa attataacac ataaagaatg taatacaata   1260
ggtatcaacg gaatgctgtt caatacaaat aaagaaggaa ctcttgcatt ttacacacca   1320
aatgatataa cattaaacaa ttctgttgca cttgatccaa ttgacatatc aatcgagctc   1380
aataaggcca aatcagatct agaagagtca aaagaatgga taagaaggtc aaatcaaaaa   1440
ctagattcca ttggaaattg gcatcaatct agcaccacaa tcataattgt tttgataatg   1500
ataattatat tgtttataat taatgtaacg ataattataa ttgcagttaa gtattacaga   1560
attcaaaaga gaaatcgagt ggatcaaaat gataaaccat atgtattaac aaacaaatga   1620
```

```

<210> SEQ ID NO 8
<211> LENGTH: 539
<212> TYPE: PRT
<213> ORGANISM: parainfluenza virus 3

<400> SEQUENCE: 8

Met Pro Thr Ser Ile Leu Leu Ile Ile Thr Thr Met Ile Met Ala Ser
1               5                   10                  15

Phe Cys Gln Ile Asp Ile Thr Lys Leu Gln His Val Gly Val Leu Val
            20                  25                  30

Asn Ser Pro Lys Gly Met Lys Ile Ser Gln Asn Phe Glu Thr Arg Tyr
        35                  40                  45

Leu Ile Leu Ser Leu Ile Pro Lys Ile Glu Asp Ser Asn Ser Cys Gly
    50                  55                  60

Asp Gln Gln Ile Lys Gln Tyr Lys Arg Leu Leu Asp Arg Leu Ile Ile
65                  70                  75                  80

Pro Leu Tyr Asp Gly Leu Arg Leu Gln Lys Asp Val Ile Val Ser Asn
                85                  90                  95

Gln Glu Ser Asn Glu Asn Thr Asp Pro Arg Thr Lys Arg Phe Phe Gly
            100                 105                 110

Gly Val Ile Gly Thr Ile Ala Leu Gly Val Ala Thr Ser Ala Gln Ile
        115                 120                 125

Thr Ala Ala Val Ala Leu Val Glu Ala Lys Gln Ala Arg Ser Asp Ile
    130                 135                 140

Glu Lys Leu Lys Glu Ala Ile Arg Asp Thr Asn Lys Ala Val Gln Ser
145                 150                 155                 160

Val Gln Ser Ser Ile Gly Asn Leu Ile Val Ala Ile Lys Ser Val Gln
                165                 170                 175

Asp Tyr Val Asn Lys Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
```

```
              195                 200                 205
Glu Leu Thr Asn Ile Phe Gly Asp Asn Ile Gly Ser Leu Gln Glu Lys
        210                 215                 220
Gly Ile Lys Leu Gln Gly Ile Ala Ser Leu Tyr Arg Thr Asn Ile Thr
225                 230                 235                 240
Glu Ile Phe Thr Thr Ser Thr Val Asp Lys Tyr Asp Ile Tyr Asp Leu
                245                 250                 255
Leu Phe Thr Glu Ser Ile Lys Val Arg Val Ile Asp Val Asp Leu Asn
            260                 265                 270
Asp Tyr Ser Ile Thr Leu Gln Val Arg Leu Pro Leu Leu Thr Arg Leu
        275                 280                 285
Leu Asn Thr Gln Ile Tyr Lys Val Asp Ser Ile Ser Tyr Asn Ile Gln
290                 295                 300
Asn Arg Glu Trp Tyr Ile Pro Leu Pro Ser His Ile Met Thr Lys Gly
305                 310                 315                 320
Ala Phe Leu Gly Gly Ala Asp Val Lys Glu Cys Ile Glu Ala Phe Ser
                325                 330                 335
Ser Tyr Ile Cys Pro Ser Asp Pro Gly Phe Val Leu Asn His Glu Met
            340                 345                 350
Glu Ser Cys Leu Ser Gly Asn Ile Ser Gln Cys Pro Arg Thr Val Val
        355                 360                 365
Thr Ser Asp Ile Val Pro Arg Tyr Ala Phe Val Asn Gly Gly Val Val
    370                 375                 380
Ala Asn Cys Ile Thr Thr Thr Cys Thr Cys Asn Gly Ile Gly Asn Arg
385                 390                 395                 400
Ile Asn Gln Pro Pro Asp Gln Gly Val Lys Ile Ile Thr His Lys Glu
                405                 410                 415
Cys Asn Thr Ile Gly Ile Asn Gly Met Leu Phe Asn Thr Asn Lys Glu
            420                 425                 430
Gly Thr Leu Ala Phe Tyr Thr Pro Asn Asp Ile Thr Leu Asn Asn Ser
        435                 440                 445
Val Ala Leu Asp Pro Ile Asp Ile Ser Ile Glu Leu Asn Lys Ala Lys
450                 455                 460
Ser Asp Leu Glu Glu Ser Lys Glu Trp Ile Arg Arg Ser Asn Gln Lys
465                 470                 475                 480
Leu Asp Ser Ile Gly Asn Trp His Gln Ser Ser Thr Thr Ile Ile Ile
                485                 490                 495
Val Leu Ile Met Ile Ile Ile Leu Phe Ile Ile Asn Val Thr Ile Ile
            500                 505                 510
Ile Ile Ala Val Lys Tyr Tyr Arg Ile Gln Lys Arg Asn Arg Val Asp
        515                 520                 525
Gln Asn Asp Lys Pro Tyr Val Leu Thr Asn Lys
530                 535

<210> SEQ ID NO 9
<211> LENGTH: 1554
<212> TYPE: DNA
<213> ORGANISM: Artificial sequence
<220> FEATURE:
<223> OTHER INFORMATION: Synthetic polynucleotide encoding RSV PreF
      analog

<400> SEQUENCE: 9
atggagctgc tgatcctgaa aaccaacgcc atcaccgcca tcctggccgc cgtgaccctg      60
tgcttcgcct cctcccagaa catcaccgag gagttctacc agtccaccct ctccgccgtg     120
```

-continued

```
tccaagggct acctgtccgc cctgcggacc ggctggtaca cctccgtgat caccatcgag    180
ctgtccaaca tcaaggaaaa caagtgcaac ggcaccgacg ccaaggtgaa gctgatcaag    240
caggagctgg acaagtacaa gagcgccgtg accgaactcc agctgctgat gcagtccacc    300
cctgccacca caacaagtt tctgggcttc ctgctgggcg tgggctccgc catcgcctcc    360
ggcatcgccg tgagcaaggt gctgcacctg gagggcgagg tgaacaagat caagagcgcc    420
ctgctgtcca ccaacaaggc cgtggtgtcc ctgtccaacg cgtgtccgt gctgacctcc    480
aaggtgctgg atctgaagaa ctacatcgac aagcagctgc tgcctatcgt gaacaagcag    540
tcctgctcca tctccaacat cgagaccgtg atcgagttcc agcagaagaa caaccggctg    600
ctggagatca cccgcgagtt ctccgtgaac gccggcgtga ccaccccgt gtccacctac    660
atgctgacca actccgagct gctgtccctg atcaacgaca tgcctatcac caacgaccag    720
aaaaaactga tgtccaacaa cgtgcagatc gtgcggcagc agtcctacag catcatgagc    780
atcatcaagg aagaggtgct ggcctacgtg gtgcagctgc ctctgtacgg cgtgatcgac    840
acccccttgct ggaagctgca cacctccccc ctgtgcacca ccaacaccaa ggagggctcc    900
aacatctgcc tgacccggac cgaccggggc tggtactgcg acaacgccgg ctccgtgtcc    960
ttcttccctc tggccgagac ctgcaaggtg cagtccaacc gggtgttctg cgacaccatg   1020
aactccctga ccctgccttc cgaggtgaac ctgtgcaaca tcgacatctt caaccccaag   1080
tacgactgca agatcatgac cagcaagacc gacgtgtcct ccagcgtgat caccctccctg   1140
ggcgccatcg tgtcctgcta cggcaagacc aagtgcaccg cctccaacaa gaaccgggga   1200
atcatcaaga ccttctccaa cggctgcgac tacgtgtcca ataagggcgt ggacaccgtg   1260
tccgtgggca cacactgta ctacgtgaat aagcaggagg caagagcct gtacgtgaag   1320
ggcgagccta tcatcaactt ctacgaccct ctggtgttcc cttccgacga gttcgacgcc   1380
tccatcagcc aggtgaacga aaagatcaac cagtccctgg ccttcatccg gaagtccgac   1440
gagaagctgc ataacgtgga ggacaagatc gaggagatcc tgtccaaaat ctaccacatc   1500
gagaacgaga tcgcccggat caagaagctg atcggcgagg cctgataatc taga           1554
```

<210> SEQ ID NO 10
<211> LENGTH: 514
<212> TYPE: PRT
<213> ORGANISM: Artificial sequence
<220> FEATURE:
<223> OTHER INFORMATION: Synthetic RSV PreF analog

<400> SEQUENCE: 10

```
Met Glu Leu Leu Ile Leu Lys Thr Asn Ala Ile Thr Ala Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95

Met Gln Ser Thr Pro Ala Thr Asn Asn Lys Phe Leu Gly Phe Leu Leu
            100                 105                 110
```

```
Gly Val Gly Ser Ala Ile Ala Ser Gly Ile Ala Val Ser Lys Val Leu
            115                 120                 125

His Leu Glu Gly Glu Val Asn Lys Ile Lys Ser Ala Leu Leu Ser Thr
    130                 135                 140

Asn Lys Ala Val Val Ser Leu Ser Asn Gly Val Ser Val Leu Thr Ser
145                 150                 155                 160

Lys Val Leu Asp Leu Lys Asn Tyr Ile Asp Lys Gln Leu Leu Pro Ile
                165                 170                 175

Val Asn Lys Gln Ser Cys Ser Ile Ser Asn Ile Glu Thr Val Ile Glu
            180                 185                 190

Phe Gln Gln Lys Asn Asn Arg Leu Leu Glu Ile Thr Arg Glu Phe Ser
            195                 200                 205

Val Asn Ala Gly Val Thr Thr Pro Val Ser Thr Tyr Met Leu Thr Asn
    210                 215                 220

Ser Glu Leu Leu Ser Leu Ile Asn Asp Met Pro Ile Thr Asn Asp Gln
225                 230                 235                 240

Lys Lys Leu Met Ser Asn Asn Val Gln Ile Val Arg Gln Gln Ser Tyr
                245                 250                 255

Ser Ile Met Ser Ile Ile Lys Glu Glu Val Leu Ala Tyr Val Val Gln
            260                 265                 270

Leu Pro Leu Tyr Gly Val Ile Asp Thr Pro Cys Trp Lys Leu His Thr
    275                 280                 285

Ser Pro Leu Cys Thr Thr Asn Thr Lys Glu Gly Ser Asn Ile Cys Leu
290                 295                 300

Thr Arg Thr Asp Arg Gly Trp Tyr Cys Asp Asn Ala Gly Ser Val Ser
305                 310                 315                 320

Phe Phe Pro Leu Ala Glu Thr Cys Lys Val Gln Ser Asn Arg Val Phe
                325                 330                 335

Cys Asp Thr Met Asn Ser Leu Thr Leu Pro Ser Glu Val Asn Leu Cys
            340                 345                 350

Asn Ile Asp Ile Phe Asn Pro Lys Tyr Asp Cys Lys Ile Met Thr Ser
            355                 360                 365

Lys Thr Asp Val Ser Ser Ser Val Ile Thr Ser Leu Gly Ala Ile Val
    370                 375                 380

Ser Cys Tyr Gly Lys Thr Lys Cys Thr Ala Ser Asn Lys Asn Arg Gly
385                 390                 395                 400

Ile Ile Lys Thr Phe Ser Asn Gly Cys Asp Tyr Val Ser Asn Lys Gly
                405                 410                 415

Val Asp Thr Val Ser Val Gly Asn Thr Leu Tyr Tyr Val Asn Lys Gln
            420                 425                 430

Glu Gly Lys Ser Leu Tyr Val Lys Gly Glu Pro Ile Ile Asn Phe Tyr
            435                 440                 445

Asp Pro Leu Val Phe Pro Ser Asp Glu Phe Asp Ala Ser Ile Ser Gln
    450                 455                 460

Val Asn Glu Lys Ile Asn Gln Ser Leu Ala Phe Ile Arg Lys Ser Asp
465                 470                 475                 480

Glu Lys Leu His Asn Val Glu Asp Lys Ile Glu Glu Ile Leu Ser Lys
                485                 490                 495

Ile Tyr His Ile Glu Asn Glu Ile Ala Arg Ile Lys Lys Leu Ile Gly
            500                 505                 510

Glu Ala
```

<210> SEQ ID NO 11
<211> LENGTH: 1536
<212> TYPE: DNA
<213> ORGANISM: Artificial sequence
<220> FEATURE:
<223> OTHER INFORMATION: Synthetic polynucleotide encoding hMPV PreF
      analog

<400> SEQUENCE: 11

| | | | | | |
|---|---|---|---|---|---|
| atgagctgga | aggtggtcat | catcttctcc | ctgctgatca | cccccagca | cggcctgaaa | 60 |
| gagtcctacc | tggaagagtc | ctgctccacc | atcaccgagg | gctacctgtc | cgtgctgcgg | 120 |
| accggctggt | acaccaatgt | gttcacccctg | gaagtgggcg | acgtggaaaa | cctgacctgc | 180 |
| tccgacggcc | ccagcctgat | caagaccgag | ctggacctga | ccaagtccgc | cctgcgcgag | 240 |
| ctgaaaaccg | tgtccgccga | ccagctggcc | agagaggaac | agatcgagaa | ccccaagcag | 300 |
| tccaagttcg | tgctgggcgc | tatcgccctg | ggcgtggcaa | ccgctgctgc | cgtgaccgct | 360 |
| ggcgtggcca | ttgccaagac | catccggctg | gaatccgaag | tgaccgccat | caagaacgcc | 420 |
| ctgaaaacca | ccaacgaggc | cgtgtccacc | ctgggcaatg | gcgtgcgggt | gctggctacc | 480 |
| gccgtgcggg | aactgaagga | cttcgtgtcc | aagaacctga | caggcgccat | caacaagaac | 540 |
| aagtgcgaca | tcgacgacct | gaagatggcc | gtcagcttca | gccagttcaa | ccggcggttc | 600 |
| ctgaacgtgg | tccgacagtt | ctccgacaac | gccggcatca | cccccgccat | ctccctggac | 660 |
| ctgatgaccc | atgccgagct | ggccagggcc | gtgtctaaca | tgcccacctc | tgccggccag | 720 |
| atcaagctga | tgctggaaaa | ccgggctatg | gtccgacgga | agggcttcgg | catcctgatc | 780 |
| ggcgtgtacg | gctcctccgt | gatctacatg | gtgcagctcc | ccatcttcgg | cgtgatcgac | 840 |
| acccccctgct | ggatcgtgaa | ggccgctccc | agctgctccg | agaagaaggg | caactacgcc | 900 |
| tgcctgctga | gagggacca | gggctggtac | tgccagaacg | ccggctccac | cgtgtactac | 960 |
| cccaacgaga | aggactgcga | gacacggggc | gaccacgtgt | tctgcgacac | cgccgctggc | 1020 |
| atcaacgtgg | ccgagcagtc | caaagagtgc | aacatcaaca | tctccaccac | caactacccc | 1080 |
| tgcaaggtgt | ccaccggcag | acacccatc | agcatggtgg | ccctgagccc | tctgggcgct | 1140 |
| ctggtggctt | gctacaaggg | cgtgtcctgc | tctatcggct | ccaacagagt | gggcatcatc | 1200 |
| aagcagctga | acaagggctg | ctcctacatc | accaaccagg | acgccgacac | cgtgaccatc | 1260 |
| gacaacaccg | tgtaccagct | gtccaaggtg | aaggcgagc | agcacgtgat | caagggcaga | 1320 |
| cccgtgtcct | ccagcttcga | ccccatcaag | ttccccgagg | accagttcaa | tgtggccctg | 1380 |
| gaccaggtgt | tcgagtccat | cgagaactcc | caggccctgg | tggaccagtc | caacagaatc | 1440 |
| ctgtcctctg | ccgaggataa | gatcgaggaa | atcctgtcca | aaatctacca | catcgagaac | 1500 |
| gagatcgccc | ggatcaagaa | gctgatcggc | gaggcc | | | 1536 |

<210> SEQ ID NO 12
<211> LENGTH: 512
<212> TYPE: PRT
<213> ORGANISM: Artificial sequence
<220> FEATURE:
<223> OTHER INFORMATION: Synthetic hMPV PreF analog

<400> SEQUENCE: 12

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe

```
                 35                  40                  45
Thr Leu Glu Val Gly Asp Val Glu Asn Leu Thr Cys Ser Asp Gly Pro
 50                  55                  60

Ser Leu Ile Lys Thr Glu Leu Asp Leu Thr Lys Ser Ala Leu Arg Glu
 65                  70                  75                  80

Leu Lys Thr Val Ser Ala Asp Gln Leu Ala Arg Glu Glu Gln Ile Glu
                 85                  90                  95

Asn Pro Lys Gln Ser Lys Phe Val Leu Gly Ala Ile Ala Leu Gly Val
                100                 105                 110

Ala Thr Ala Ala Ala Val Thr Ala Gly Val Ala Ile Ala Lys Thr Ile
                115                 120                 125

Arg Leu Glu Ser Glu Val Thr Ala Ile Lys Asn Ala Leu Lys Thr Thr
                130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
                180                 185                 190

Phe Ser Gln Phe Asn Arg Arg Phe Leu Asn Val Val Arg Gln Phe Ser
                195                 200                 205

Asp Asn Ala Gly Ile Thr Pro Ala Ile Ser Leu Asp Leu Met Thr Asp
210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
                260                 265                 270

Leu Pro Ile Phe Gly Val Ile Asp Thr Pro Cys Trp Ile Val Lys Ala
                275                 280                 285

Ala Pro Ser Cys Ser Glu Lys Lys Gly Asn Tyr Ala Cys Leu Leu Arg
                290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
                340                 345                 350

Asn Ile Ser Thr Thr Asn Tyr Pro Cys Lys Val Ser Thr Gly Arg His
                355                 360                 365

Pro Ile Ser Met Val Ala Leu Ser Pro Leu Gly Ala Leu Val Ala Cys
                370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
                420                 425                 430

Glu Gln His Val Ile Lys Gly Arg Pro Val Ser Ser Ser Phe Asp Pro
                435                 440                 445

Ile Lys Phe Pro Glu Asp Gln Phe Asn Val Ala Leu Asp Gln Val Phe
                450                 455                 460
```

```
Glu Ser Ile Glu Asn Ser Gln Ala Leu Val Asp Gln Ser Asn Arg Ile
465                 470                 475                 480

Leu Ser Ser Ala Glu Asp Lys Ile Glu

-continued

<223> OTHER INFORMATION: Synthetic PIV-3 PreF analog

<400> SEQUENCE: 14

```
Met Pro Thr Ser Ile Leu Leu Ile Ile Thr Thr Met Ile Met Ala Ser
1               5                   10                  15

Phe Cys Gln Ile Asp Ile Thr Lys Leu Gln His Val Gly Val Leu Val
            20                  25                  30

Asn Ser Pro Lys Gly Met Lys Ile Ser Gln Asn Phe Glu Thr Arg Tyr
        35                  40                  45

Leu Ile Leu Ser Leu Ile Pro Lys Ile Glu Asp Ser Asn Ser Cys Gly
    50                  55                  60

Asp Gln Gln Ile Lys Gln Tyr Lys Arg Leu Leu Asp Arg Leu Ile Ile
65                  70                  75                  80

Pro Leu Tyr Asp Gly Leu Arg Leu Gln Lys Asp Val Ile Val Ser Asn
                85                  90                  95

Gln Glu Ser Asn Glu Asn Thr Asp Pro Lys Thr Lys Lys Phe Phe Gly
            100                 105                 110

Gly Val Ile Gly Thr Ile Ala Leu Gly Val Ala Thr Ser Ala Gln Ile
        115                 120                 125

Thr Ala Ala Val Ala Leu Val Glu Ala Lys Gln Ala Arg Ser Asp Ile
    130                 135                 140

Glu Lys Leu Lys Glu Ala Ile Arg Asp Thr Asn Lys Ala Val Gln Ser
145                 150                 155                 160

Val Gln Ser Ser Ile Gly Asn Leu Ile Val Ala Ile Lys Ser Val Gln
                165                 170                 175

Asp Tyr Val Asn Lys Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Ser Leu Gln Glu Lys
    210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
            260                 265                 270

Asp Tyr Ser Ile Thr Leu Gln Val Arg Leu Pro Leu Leu Thr Arg Leu
        275                 280                 285

Leu Asn Thr Gln Ile Tyr Lys Val Asp Ser Ile Ser Tyr Asn Ile Gln
    290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Met
            340                 345                 350

Glu Ser Cys Leu Ser Gly Asn Ile Ser Gln Cys Pro Arg Thr Val Val
        355                 360                 365

Thr Ser Asp Ile Val Pro Arg Tyr Ala Phe Val Asn Gly Gly Val Val
    370                 375                 380

Ala Asn Cys Ile Thr Thr Thr Cys Thr Cys Asn Gly Ile Gly Asn Arg
385                 390                 395                 400
```

```
Ile Asn Gln Pro Pro Asp Gln Gly Val Lys Ile Ile Thr His Lys Glu
                405                 410                 415

Cys Asn Thr Ile Gly Ile Asn Gly Met Leu Phe Asn Thr Asn Lys Glu
            420                 425                 430

Gly Thr Leu Ala Phe Tyr Thr Pro Asn Asp Ile Thr Leu Asn Asn Ser
        435                 440                 445

Val Ala Leu Asp Pro Ile Asp Ile Ser Ile Glu Leu Asn Lys Ala Lys
    450                 455                 460

Ser Asp Leu Glu Glu Ser Lys Glu Trp Ile Arg Arg Ser Asn Gln Lys
465                 470                 475                 480

Leu Asp Ser Ile Glu Asp Lys Ile Glu Glu Ile Leu Ser Lys Ile Tyr
            485                 490                 495

His Ile Glu Asn Glu Ile Ala Arg Ile Lys Lys Leu Ile Gly Glu Ala
                500                 505                 510

<210> SEQ ID NO 15
<211> LENGTH: 28
<212> TYPE: PRT
<213> ORGANISM: Artificial sequence
<220> FEATURE:
<223> OTHER INFORMATION: Synthetic isoleucine zipper

<400> SEQUENCE: 15

Glu Asp Lys Ile Glu Glu Ile Leu Ser Lys Ile Tyr His Ile Glu Asn
1               5                   10                  15

Glu Ile Ala Arg Ile Lys Lys Leu Ile Gly Glu Ala
            20                  25
```